US 10,526,355 B2

(12) United States Patent
Eißmann et al.

(10) Patent No.: US 10,526,355 B2
(45) Date of Patent: Jan. 7, 2020

(54) HARDENER AND CURE ACCELERANT WITH FLAME RETARDANCY EFFECT FOR CURING EPOXY RESINS (II)

(71) Applicant: ALZCHEM AG, Trostberg (DE)

(72) Inventors: Frank Eißmann, Tacherting (DE); Martin Ebner, Kissing (DE); Hans-Peter Krimmer, Kirchweidach (DE); Doris Krammer, Kienberg (DE)

(73) Assignee: ALZCHEM AG, Trostberg (DE)

( * ) Notice: Subject to any disclaimer, the term of this patent is extended or adjusted under 35 U.S.C. 154(b) by 0 days.

(21) Appl. No.: 15/566,837

(22) PCT Filed: Apr. 14, 2016

(86) PCT No.: PCT/EP2016/058249
§ 371 (c)(1),
(2) Date: Oct. 16, 2017

(87) PCT Pub. No.: WO2016/166229
PCT Pub. Date: Oct. 20, 2016

(65) Prior Publication Data
US 2018/0105545 A1    Apr. 19, 2018

(30) Foreign Application Priority Data
Apr. 17, 2015  (DE) .................. 10 2015 004 955

(51) Int. Cl.
| | | |
|---|---|---|
| C07F 9/141 | (2006.01) | |
| C09K 21/12 | (2006.01) | |
| C09J 163/00 | (2006.01) | |
| C09J 9/00 | (2006.01) | |
| C09D 163/00 | (2006.01) | |
| C09D 5/18 | (2006.01) | |
| C08J 5/24 | (2006.01) | |
| C08G 59/44 | (2006.01) | |
| C07F 9/40 | (2006.01) | |
| C07F 9/32 | (2006.01) | |
| C07F 9/165 | (2006.01) | |
| C08G 59/68 | (2006.01) | |
| C08G 59/40 | (2006.01) | |
| C08G 59/24 | (2006.01) | |

(52) U.S. Cl.
CPC ............. *C07F 9/141* (2013.01); *C07F 9/165* (2013.01); *C07F 9/3258* (2013.01); *C07F 9/4071* (2013.01); *C08G 59/44* (2013.01); *C08J 5/24* (2013.01); *C09D 5/18* (2013.01); *C09D 163/00* (2013.01); *C09J 9/00* (2013.01); *C09J 163/00* (2013.01); *C09K 21/12* (2013.01); *C08G 2150/00* (2013.01); *C08G 2150/20* (2013.01); *C08G 2170/00* (2013.01); *C08G 2190/00* (2013.01); *C08J 2363/00* (2013.01)

(58) Field of Classification Search
None
See application file for complete search history.

(56) References Cited

U.S. PATENT DOCUMENTS

| | | | | |
|---|---|---|---|---|
| 3,383,194 A | * | 5/1968 | Young .................. | C07F 9/18 504/194 |
| 3,857,907 A | * | 12/1974 | Martin .................. | C07F 9/097 558/115 |
| 5,698,002 A | * | 12/1997 | Hudson .................. | B01J 2/006 71/28 |

FOREIGN PATENT DOCUMENTS

| | | |
|---|---|---|
| EP | 2036911 A1 | 3/2009 |
| JP | 2012177777 A * | 9/2012 |

OTHER PUBLICATIONS

International Application No. PCT/EP2016/058249, International Search Report and Written Opinion dated Jun. 17, 2016, 9 pages.
Ping et al., "Epoxy Resin and Its Application", Chemical Industry Press, Feb. 2004, p. 46, 14 pages (1 page of English translation and 13 pages of Original document).

* cited by examiner

Primary Examiner — Randy P Gulakowski
Assistant Examiner — Ha S Nguyen
(74) Attorney, Agent, or Firm — Kilpatrick Townsend & Stockton LLP

(57) ABSTRACT

The present invention relates to novel hardeners for curing epoxy resins and to cure accelerators for the accelerated curing of epoxy resins comprising, in each case, at least one compound from the group of esters of phosphorus-containing acids according to Formula (I), wherein there applies to Formula (I):

Formula (I)

$$[R^3]_n-\overset{X}{\underset{\parallel}{P}}-\left[O-\left[\begin{array}{c}H\\H\end{array}\right]_p-\begin{array}{c}\phantom{x}\\\phantom{x}\end{array}\overset{R^6}{\phantom{x}}\underset{H}{N}-\overset{O}{\underset{\parallel}{C}}-\underset{R^2}{N}-R^1\right]_m$$

wherein there applies to the radicals $R^1$, $R^2$, $R^3$, $R^6$, X and indices m, n, p, simultaneously or independently of one another:
$R^1$, $R^2$=simultaneously or independently of one another, hydrogen or alkyl,
$R^3$=alkyl, aryl, —O-alkyl, —O-aryl, —O-alkylaryl or —O-arylalkyl,
$R^6$=hydrogen, alkyl or —NHC(O)NR$^1$R$^2$,
X=oxygen or sulphur,
m=1, 2 or 3,
n=0, 1 or 2, wherein there applies: m+n=3
p=0, 1 or 2.

17 Claims, No Drawings

HARDENER AND CURE ACCELERANT WITH FLAME RETARDANCY EFFECT FOR CURING EPOXY RESINS (II)

CROSS REFERENCE TO RELATED APPLICATIONS

This application is a national stage application under 35 U.S.C. § 371 of PCT/EP2016/058249 filed Apr. 14, 2016, which claims priority to German application no. 10 2015 004 955.0 filed Apr. 17, 2015, the disclosures of which are hereby incorporated by reference herein in their entireties.

The present invention relates to novel hardeners and cure accelerants for the curing and accelerated curing of epoxy resins as well as to epoxy resin compositions comprising these hardeners or cure accelerants.

The use of thermosetting epoxy resins is widespread due to their good chemical resistance, their very good thermal and dynamic-mechanical properties as well as their high electrical insulation capacity. Moreover, epoxy resins exhibit good adhesion to many substrates and are therefore highly suitable for use in fibre composites and as adhesives.

The curing of epoxy resins proceeds according to different mechanisms. Apart from curing with phenols or anhydrides, curing is frequently carried out with amines. These materials are generally liquid and can be mixed very well with epoxy resins. Because of their high reactivity and therefore very low latency, epoxy resin compositions of this type have a two-component configuration. This means that the resin (A-component) and hardener (B-component) are stored separately and are only mixed in the correct ratio shortly before use. "Latent" means here that a mixture of the individual components, namely the A-component and the B-component, is present in a stable manner under defined storage conditions. These two-component resin formulations are also designated as cold-curing resin formulations, the hardeners used for this generally being selected from the group of amines or amidoamines.

Single-component, hot-curing epoxy resin formulations, on the other hand, are completely pre-assembled ready for use, in other words, the epoxy resin and hardener are present factory-mixed. Mixing errors of the individual components during use on site are therefore ruled out. Latent hardener systems, which do not react with the epoxy resin at room temperature (are storable) but readily fully react under heating, depending on the energy input, are a prerequisite for this. Dicyandiamide, for example, is a particularly suitable and also economical hardener for single-component epoxy resin formulations of this type. Under environmental conditions, corresponding resin-hardener mixtures can be stored for up to twelve (12) months ready for use.

Because of the wide applicability of epoxy resins, in particular also as a surface layer, queries about the safety of the products produced from or with epoxy resins are intensifying and not only from legislative bodies. Thus, in particular, the demand for flame retarding or a flame retardancy effect of the epoxy resins has become a particular interest for users. This demand has top priority in many sectors because of the danger to people and material assets. To be mentioned in this context are, for example, construction materials for aircraft, ship, motor vehicle and rail vehicle construction, but also surface seals for materials exposed to high thermal stress, such as, for example, sealing compounds for printed circuit boards or windings of electric motors.

To assess the combustion behaviour, the materials have to pass the most varied material tests, depending on the area of use. Combustibility under normal atmosphere (about 21% oxygen), flame extinction, but also smoke behaviour are substantially investigated here. The requirements to be tested by these material tests can only be met with difficulty. Many known flame-retarding or fame-resistant epoxy resin materials in technical use therefore contain up to 20% bromine in the form of brominated resin components. In addition, substantial quantities of metals, for example in the form of antimony trioxide or aluminium hydroxide, are often used as synergistically acting flame retardants. The problem with these compounds is that, on the one hand, they are excellently effective as flame retardants but, on the other hand, are to be classified as environmentally unfriendly or damaging to human health. In addition, the disposal of old bromine-containing materials increasingly poses substantial problems.

For these reasons, there has been no lack of tests to replace bromine-containing flame retardants by less problematic substances. Examples to be mentioned as alternatives for halogen-containing flame retardants are salt-type flame retardants, such as, in particular, melamine phosphate, and phosphorus-containing flame retardants, in particular based on 9,10-dihydro-9-oxa-10-phosphaphenanthrene-10-oxide (DOPO) and derivatives thereof (cf. also M. Rakotomalala, S. Wagner and M. Döring, *Materials* 2010, 3, 4300-4327).

Furthermore, reactive organic phosphorus compounds such as epoxy group-containing phosphorus compounds were also proposed for the flame-retarding adjustment of epoxy resins. Epoxy resin mixtures for use in printed circuit board materials are known from European patent application EP 384 940 A1, which contain a phosphorus-free polyepoxy resin in combination with an epoxy group-containing phosphorus compound and a special aromatic polyamine in the form of an isocyanuric acid derivative as the hardener.

Epoxy resin mixtures are also known from the German specifications laid open to public inspection DE 43 08 184 A1 and DE 43 08 187 A1, which contain a phosphorus-modified epoxy resin with an epoxy value of 0.02 to 1 mol/100 g in combination with the above-mentioned polyamine. The phosphorus-modified epoxy resins are constructed in this case from structural units, which, on the one hand, are derived from polyepoxy compounds with at least two epoxy groups per molecule and, on the other hand, from phosphinic, phosphonic and pyrophosphonic acids or phosphonic acid semi-esters or from phosphinic and phosphonic acid anhydrides.

Further epoxy resin mixtures for producing prepregs or composite materials containing phosphorus-modified epoxy resins, aromatic amines as hardeners and at least one cure accelerant are known from international patent applications WO 96/07685 A1 and WO 96/07686 A1.

There has also been no lack of tests to develop cast resins based on phosphorus components. Thus, for example, anhydridically curable epoxy cast resins are known, which contain phosphonic acid anhydride as the hardener or are obtained by modifying epoxy resin or hardener components with phosphorus compounds (cf. DE 42 37 132 C1, DE 195 06 010 A1). These cast resins are predominantly highly viscous and can only be processed without solvents at temperatures >60° C.; temperatures of >80° C. are required for curing.

Furthermore, phosphoric acid amides, which can be used in epoxy resins, are known from international patent application WO 2009/0077796 A1.

Even if, in the very recent past, substantial progress has been achieved in the field of halogen-free flame retardants that can be used in epoxy resins, no halogen-free hardeners or cure accelerants for curing epoxy resins have hitherto been known, which, as an integral component of the polymer network of the cured epoxy resin, exert a flame retardancy effect.

The present invention is therefore based on the object of providing novel compounds, which can be used for curing epoxy resins and epoxy resin compositions, in particular as hardeners and/or cure accelerants, and which, once they have been incorporated in epoxy resin compositions, additionally provide a flame retardancy effect, so the products produced from or with the epoxy resin composition can be classified as flame-retarding or flame retardant. Furthermore, the necessity exists here for providing such hardeners and cure accelerants with a flame retardancy effect, which can be classified as latent and therefore they have a high storage stability in epoxy resins below the curing temperature and a high reactivity at the curing temperature to allow a complete cross-linking of the epoxy resin.

These objects are achieved by a hardener according to claim 1 and a cure accelerant according to claim 2. Advantageous embodiments of the invention are specified in the sub-claims, which can optionally be combined with one another.

Accordingly, according to a first embodiment, a hardener for curing epoxy resins comprising at least one compound from the group of esters of phosphorus-containing acids according to Formula (I) is the subject of the present invention, wherein there applies to Formula (I):

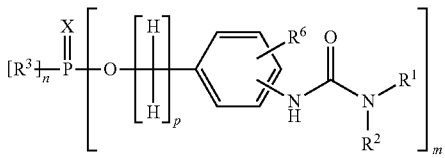

Formula (I)

wherein there applies to the radicals $R^1$, $R^2$, $R^3$, $R^6$, X and indices m, n, p, simultaneously or independently:
$R^1$, $R^2$=simultaneously or independently of one another, hydrogen or alkyl,
$R^3$=alkyl, aryl, —O-alkyl, —O-aryl, —O-alkylaryl or —O-arylalkyl,
$R^6$=hydrogen, alkyl or —NHC(O)NR$^1$R$^2$,
X=oxygen or sulphur,
m=1, 2 or 3,
n=0, 1 or 2, wherein there applies: m+n=3
p=0, 1 or 2.

According to a second embodiment, a cure accelerant for the accelerated curing of epoxy resins comprising at least one compound from the group of esters of phosphorus-containing acids according to Formula (I) is also the subject of the present invention, wherein there applies to Formula (I):

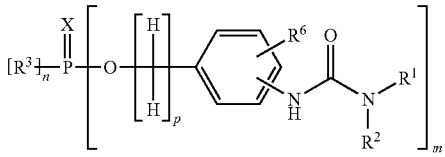

Formula (I)

wherein there applies to the radicals $R^1$, $R^2$, $R^3$, $R^6$, X and indices m, n, p, simultaneously or independently of one another:
$R^1$, $R^2$=simultaneously or independently of one another, hydrogen or alkyl,
$R^3$=alkyl, aryl, —O-alkyl, —O-aryl, —O-alkylaryl or —O-arylalkyl,
$R^6$=hydrogen, alkyl or —NHC(O)NR$^1$R$^2$,
X=oxygen or sulphur,
m=1, 2 or 3,
n=0, 1 or 2, wherein there applies: m+n=3
p=0, 1 or 2.

Preferred here are hardeners and cure accelerants comprising, in each case, at least one compound form the group of esters of phosphorus-containing acids according to Formula (I), to the index p of which there applies:
p=0 or 1, in particular 0.

Therefore, according to the present invention, a hardener and/or a cure accelerant comprising, in each case, at least one compound from the group of esters of phosphorus-containing acids according to Formula (Ia) are preferred, wherein there applies to Formula (Ia):

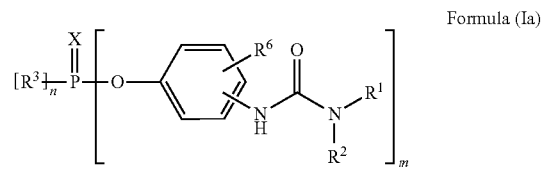

Formula (Ia)

wherein there applies to the radicals $R^1$, $R^2$, $R^3$, $R^6$, X and indices m, n, simultaneously or independently of one another:
$R^1$, $R^2$=simultaneously or independently of one another, hydrogen or alkyl
$R^3$=alkyl, aryl, —O-alkyl, —O-aryl, —O-alkylaryl or —O-arylalkyl,
$R^6$=hydrogen, alkyl or —NHC(O)NR$^1$R$^2$,
X=sulphur or oxygen,
m=1, 2 or 3,
n=0, 1 or 2, wherein there applies: m+n=3.

Furthermore, hardeners and cure accelerants comprising, in each case, at least one compound from the group of esters of phosphorus-containing acids according to Formula (I) or Formula (Ia) are preferred, to the radicals $R^3$ of which there applies:
$R^3$=aryl, —O-aryl or —O-alkylaryl.

Further preferred are hardeners and cure accelerants comprising, in each case, at least one compound from the group of esters of phosphorus-containing acids according to Formula (I) or Formula (Ia), to the radicals $R^6$ of which there applies:
$R^6$=hydrogen or alkyl.

Further preferred are hardeners and cure accelerants comprising, in each case, at least one compound from the group of esters of phosphorus-containing acids according to Formula (I) or Formula (Ia), to the radical X of which there applies:
X=oxygen.

Further preferred here are hardeners and cure accelerants comprising, in each case, at least one compound from the group of esters of phosphorus-containing acids according to Formula (I) or Formula (Ia), to the radicals $R^1$, $R^2$ of which there applies, simultaneously or independently of one another:

$R^1$, $R^2$=simultaneously or independently of one another alkyl, in particular simultaneously or independently of one another, methyl or ethyl, in particular simultaneously methyl or ethyl.

Particularly preferred are hardeners and cure accelerants comprising, in each case, at least one compound from the group of esters of phosphorus-containing acids according to Formula (I), to the radicals $R^1$, $R^2$, $R^6$, X of which and indices m, n, p in Formula (I), there applies, simultaneously or independently of one another:
$R^1$, $R^2$=simultaneously or independently of one another, methyl or ethyl,
$R^3$=aryl, —O-aryl or —O-alkylaryl,
$R^6$=hydrogen or alkyl,
X=sulphur or oxygen,
m=1, 2 or 3,
n=0, 1 or 2, wherein there applies: m+n=3
p=0.

Particularly preferred are hardeners and cure accelerants comprising, in each case, at least one compound from the group of esters of phosphorus-containing acids according to Formula (Ia), to the radicals $R^1$, $R^2$, $R^6$, X of which and indices m, n, p in Formula (Ia), there applies, simultaneously or independently of one another:
$R^1$, $R^2$=simultaneously or independently of one another, methyl or ethyl,
$R^3$=aryl, —O-aryl or —O-alkylaryl,
$R^6$=hydrogen or alkyl,
X=sulphur or oxygen,
m=1, 2 or 3,
n=0, 1 or 2, wherein there applies: m+n=3.

According to the present invention, alkyl means here a linear or branched, monovalent radical, which has the general formula $C_nH_{2n+1}$, wherein n expresses the number of carbon atoms of the radical and n means, in particular, a number from 1 to 10, preferably 1 to 5, particularly preferably 1 or 2. Thus, alkyl according to the present invention may in particular mean methyl, ethyl, n-propyl, n-butyl, n-pentyl, n-hexyl, n-heptyl, n-octyl, n-nonyl, n-decyl, 1-methylethyl, 1-methylpropyl, 1-methylbutyl, 1-methylpentyl, 1-methylhexyl, 1-methylheptyl, 1-methyloctyl, 1-methylnonyl, 1-ethylpropyl, 1-ethylbutyl, 1-ethylpentyl, 1-ethylhexyl, 1-ethylheptyl, 1-ethyloctyl, 2-methylpropyl, 2-methylbutyl, 2-methylpentyl, 2-methylhexyl, 2-methylheptyl, 2-methyloctyl, 2-methylnonyl, 2-ethylbutyl, 2-ethylpentyl, 2-ethylhexyl, 2-ethylheptyl, 2-ethyloctyl, 1,1-dimethylethyl, 1,1-dimethylpropyl, 1,1-dimethylbutyl, 1,1-dimethylpentyl, 1,1-dimethylhexyl, 1,1-dimethylheptyl, 1,1-dimethyloctyl, 1,2-dimethylpropyl, 1,2-dimethylbutyl, 1,2-dimethylpentyl, 1,2-dimethylhexyl, 1,2-dimethylheptyl, 1,2-dimethyloctyl, 2-ethyl-1-methylbutyl, 2-ethyl-1-methylpentyl, 2-ethyl-1-methylhexyl, 2-ethyl-1-methylheptyl, 1-ethyl-2-methylpropyl, 1-ethyl-2-methylbutyl, 1-ethyl-2-methylpentyl, 1-ethyl-2-methylhexyl or 1-ethyl-2-methylheptyl.

According to the present invention, alkyl particularly preferably means methyl, ethyl, 1-methylethyl, n-propyl, n-butyl, 2-methylbutyl or 1,1-dimethylethyl. Most preferably alkyl means, according to the present invention, methyl or ethyl.

According to the present invention, aryl means a monovalent aromatic radical with, in particular, 3 to 20 carbon atoms, preferably 6 to 20 carbon atoms, particularly preferably 6 carbon atoms, which may be monocyclic, bicyclic or polycyclic. Therefore, aryl according to the present invention may, in particular, mean phenyl, naphthyl, anthryl, phenanthryl, pyrenyl or perylenyl.

According to the present invention, aryl particularly preferably means phenyl.

According to the present invention, alkylaryl means an aryl radical of the meaning expressed above with, in particular, 3 to 20 carbon atoms, which is in turn singly or repeatedly substituted with an alkyl radical of the meaning expressed above with, in particular, 1 to 10 carbon atoms, the binding of the alkylaryl radical to the basic framework being localised on the aromatic core. Thus, alkylaryl according to the present invention may, in particular, mean tolyl, xylyl, pseudocumyl or mesityl.

According to the present invention, alkylaryl particularly preferably means tolyl.

According to the present invention, arylalkyl means an alkyl radical of the meaning expressed above, which is substituted with an aryl radical of the meaning expressed above, the binding of the arylalkyl radical to the basic framework being localised on the alkyl radical. Thus, arylalkyl according to the present invention may, in particular, mean benzyl, 1-phenylethyl or 1-methyl-1-phenylethyl.

According to the present invention, arylalkyl particularly preferably means benzyl.

According to the present invention, —NHC(O)$NR^1R^2$ means a carbamoyl amino radical, which is substituted on the carbamoyl nitrogen with the radicals $R^1$ and $R^2$, wherein $R^1$ and $R^2$ have the meanings expressed above, and which is bound to the basic framework by the amino nitrogen.

According to the present invention, —NHC(O)$NR^1R^2$ particularly preferably means (dimethylcarbamoyl) amino.

According to the present invention, —O-alkyl means an alkoxy radical, this alkoxy radical being bound to the basic framework by the oxygen, and wherein alkyl otherwise has the meaning expressed above. Thus —O-alkyl may mean, in particular, methoxy, ethoxy, n-propoxy or 1-methylethoxy.

According to the present invention, —O-alkyl particularly preferably means methoxy or ethoxy.

According to the present invention, —O-aryl means an aryloxy radical, wherein this aryloxy radical is bound to the basic framework by the oxygen and wherein aryl otherwise has the meaning expressed above. Thus, —O-aryl may, in particular, mean phenoxy or naphthoxy.

According to the present invention, —O-aryl particularly preferably means phenoxy.

According to the present invention, —O-alkylaryl means an alkylaryloxy radical, wherein this alkylaryloxy radical is bound to the basic framework by the oxygen, and wherein the binding of the alkylaryl radical to the oxygen is localised on the aromatic core of the alkylaryl radical, and wherein alkylaryl otherwise has the meaning expressed above. Thus, —O-alkylaryl may, in particular, mean tolyloxy or xylyloxy.

According to the present invention, —O-alkylaryl particularly preferably means tolyloxy.

According to the present invention, —O-arylalkyl means an arylalkoxy radical, wherein this arylalkoxy radical is bound to the basic framework by the oxygen, and wherein the binding of the arylalkyl radical to the oxygen is localised on the alkyl radical of the arylalkyl radical, and wherein arylalkyl otherwise has the meaning expressed above. Thus, —O-arylalkyl may, in particular, mean benzyloxy.

According to the present invention, —O-arylalkyl particularly preferably means benzyloxy.

Experimental investigations have shown that these compounds from the group of esters of phosphorus-containing acids can be excellently used for curing epoxy resins. In further investigations, it has also been found that these compounds can be used as hardeners for curing epoxy resins and also as cure accelerants for the accelerated curing of epoxy resins, which, for example, are cured with a conventional dicyandiamide hardener. Thus, it has completely surprisingly been found that the compounds according to the invention can be used, independently of one another, both as hardeners and also as cure accelerants in combination with known hardeners. The compounds thus provided react as hardeners or as cure accelerants with the epoxy resin to be cured and are therefore a component of the polymer network of the cured epoxy resin.

Thus, according to the present invention, depending on the radical X, the indices m and n and the type of radical $R^3$, in particular hardeners and cure accelerants are the subject of the present invention, which, in each case, comprise at least one compound selected from the group of phosphoric acid esters and thiophosphoric acid esters according to Formula (I), or, in each case, at least one compound selected from the group of phosphonates and thiophosphonates (esters of organophosphoric compounds of phosphonic acid or their thio derivatives) according to Formula (I), or, in each case, at least one compound selected from the group of phosphinates and thiophosphinates (esters of organophosphoric compounds of phosphinic acid or their thio derivatives) according to Formula (I).

Phosphoric acid esters and thiophosphoric acid esters are preferred according to the present invention. Thus, according to a further embodiment, a hardener and/or a cure accelerant comprising, in each case, at least one compound selected from the group of phosphoric acid esters and thiophosphoric acid esters according to Formula (I) are particularly preferred, to the radicals $R^1$, $R^2$, $R^3$, $R^6$, X of which and indices m, n, p, there applies, simultaneously or independently of one another:
  $R^1$, $R^2$=simultaneously or independently of one another, hydrogen or alkyl,
  $R^3$=—O-alkyl, —O-aryl, —O-alkylaryl or —O-arylalkyl,
  $R^6$=hydrogen, alkyl or —NHC(O)NR$^1$R$^2$,
  X=oxygen or sulphur,
  m=1, 2 or 3,
  n=0, 1 or 2, wherein there applies: m+n=3
  p=0, 1 or 2.

Particularly preferred here are phosphoric acid esters and thiophosphoric acid esters according to Formula (I) to the index p of which there applies:
  p=0 or 1, in particular 0.

Therefore, according to the present invention, a hardener and/or a cure accelerant comprising, in each case, at least one compound selected from the group of phosphoric acid esters and thiophosphoric acid esters according to Formula (Ia) are further preferred, wherein there applies to Formula (Ia):

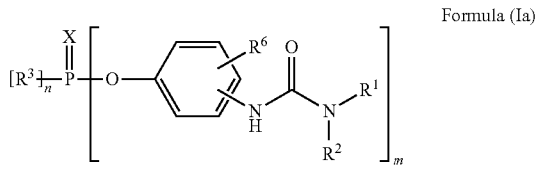

Formula (Ia)

wherein there applies to the radicals $R^1$, $R^2$, $R^3$, $R^6$, X thereof and indices m, n, simultaneously or independently of one another:
  $R^1$, $R^2$=simultaneously or independently of one another, hydrogen or alkyl,
  $R^3$=—O-aryl, —O-alkylaryl or —O-arylalkyl,
  $R^6$=hydrogen, alkyl or —NHC(O)NR$^1$R$^2$,
  X=sulphur or oxygen,
  m=1, 2 or 3,
  n=0, 1 or 2, wherein there applies: m+n=3.

Further preferred are a hardener and/or a cure accelerant comprising, in each case, at least one compound selected from the group of phosphoric acid esters or thiophosphoric acid esters according to Formula (I), to the radicals $R^1$, $R^2$, $R^3$, $R^6$, X of which and indices m, n, p, there applies, simultaneously or independently of one another:
  $R^1$, $R^2$=simultaneously or independently of one another, alkyl, in particular methyl or ethyl
  $R^3$=—O-aryl or —O-alkylaryl, in particular phenoxy or tolyloxy,
  $R^6$=hydrogen or alkyl, in particular hydrogen or methyl,
  X=oxygen or sulphur,
  m=1, 2 or 3,
  n=0, 1 or 2, wherein there applies: m+n=3
  p=0 or 1, in particular 0.

Further preferred are a hardener and/or a cure accelerant comprising, in each case, at least one compound selected from the group of phosphoric acid esters or thiophosphoric acid esters according to Formula (I), to the radicals $R^1$, $R^2$, $R^6$, X of which and indices m, n, p, there applies, simultaneously or independently of one another:
  $R^1$, $R^2$=simultaneously or independently of one another, methyl or ethyl,
  $R^6$=hydrogen or alkyl, in particular hydrogen or methyl,
  X=sulphur or oxygen,
  m=3,
  n=p=0.

Particularly preferred are a hardener and/or a cure accelerant comprising, in each case, at least one compound selected from the group of phosphoric acid esters or thiophosphoric acid esters according to Formula (Ia), to the radicals $R^1$, $R^2$, $R^6$, X of which and indices m, n, there applies, simultaneously or independently of one another:
  $R^1$, $R^2$=simultaneously or independently of one another, methyl or ethyl,
  $R^6$=hydrogen or methyl,
  X=sulphur or oxygen,
  m=3,
  n=0.

Alternatively preferred according to the present invention are phosphonates and thiophosphonates. Therefore, according to a further embodiment, a hardener and/or a cure accelerant comprising, in each case, at least one compound selected from the group of phosphonates and thiophosphonates according to Formula (I) are particularly preferred, to the radicals $R^1$, $R^2$, $R^3$, $R^6$, X of which and indices m, n, p, there applies, simultaneously or independently of one another:
  $R^1$, $R^2$=simultaneously or independently of one another, hydrogen or alkyl,
  $R^3$=alkyl or aryl,
  $R^6$=hydrogen, alkyl or —NHC(O)NR$^1$R$^2$,
  X=oxygen or sulphur,
  m=2,
  n=1,
  p=0, 1 or 2.

Particularly preferred here are phosphonates and thiophosphonates according to Formula (I), to the index p of which there applies:
  p=0 or 1, in particular 0.

Thus, according to the present invention further preferred are a hardener and/or a cure accelerant comprising, in each case, at least one compound selected from the group of phosphonates and thiophosphonates according to Formula (Ia), wherein there applies to Formula (Ia):

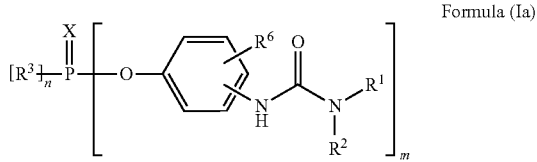

Formula (Ia)

wherein there applies to the radicals $R^1$, $R^2$, $R^3$, $R^6$, X thereof and indices m, n, simultaneously or independently of one another:
$R^1$, $R^2$=simultaneously or independently of one another, hydrogen or alkyl, in particular methyl or ethyl,
$R^3$=alkyl or aryl, in particular phenyl,
$R^6$=hydrogen, alkyl or —NHC(O)NR$^1$R$^2$, in particular hydrogen or methyl,
X=sulphur or oxygen,
m=2,
n=1.

Further preferred according to the present invention are a hardener and/or a cure accelerant comprising, in each case, at least one compound selected from the group of phosphonates and thiophosphonates according to Formula (I), to the radicals $R^1$, $R^2$, $R^3$, $R^6$, X of which and indices m, n, p, there applies, simultaneously or independently of one another:
$R^1$, $R^2$=simultaneously or independently of one another, alkyl, in particular methyl or ethyl,
$R^3$=aryl, in particular phenyl,
$R^6$=hydrogen or alkyl, in particular hydrogen or methyl,
X=oxygen or sulphur,
m=2,
n=1,
p=0 or 1, in particular 0.

In addition, alternatively preferred according to the present invention are phosphinates and thiophosphinates. Therefore, according to a further embodiment, particularly preferred are a hardener and/or a cure accelerant comprising, in each case, at least one compound selected from the group of phosphinates and thiophosphinates according to Formula (I), to the radicals $R^1$, $R^2$, $R^3$, $R^6$, X of which and indices m, n, p, there applies, simultaneously or independently of one another:
$R^1$, $R^2$=simultaneously or independently of one another, hydrogen or alkyl,
$R^3$=alkyl or aryl,
$R^6$=hydrogen, alkyl or —NHC(O)NR$^1$R$^2$,
X=oxygen or sulphur,
m=1,
n=2,
p=0, 1 or 2.

Particularly preferred here are phosphinates and thiophosphinates according to Formula (I), to the index p of which there applies:
p=0 or 1, in particular 0.

Therefore, according to the present invention, further preferred are a hardener and/or a cure accelerant comprising, in each case, at least one compound selected from the group of phosphinates and thiophosphinates according to Formula (Ia).

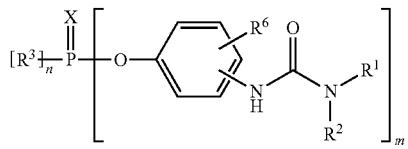

Formula (Ia)

wherein there applies to the radicals $R^1$, $R^2$, $R^3$, $R^6$, X and indices m, n, simultaneously or independently of one another:
$R^1$, $R^2$=simultaneously or independently of one another, hydrogen, methyl or ethyl,
$R^3$=alkyl or aryl,
$R^6$=hydrogen, alkyl or —NHC(O)NR$^1$R$^2$,
X=sulphur or oxygen,
m=1,
n=2.

Further preferred according to the present invention are a hardener and/or a cure accelerant comprising, in each case, at least one compound selected from the group of phosphinates and thiophosphinates according to Formula (I), to the radicals $R^1$, $R^2$, $R^3$, $R^6$, X of which and indices m, n, p, there applies, simultaneously or independently of one another:
$R^1$, $R^2$=simultaneously or independently of one another, alkyl, in particular methyl or ethyl,
$R^3$=aryl, in particular phenyl,
$R^6$=hydrogen or alkyl, in particular hydrogen or methyl,
X=oxygen or sulphur,
m=1,
n=2,
p=0 or 1, in particular 0.

Regardless of which oxygen stage the phosphorus in Formula (I) or Formula (Ia) has, it is important in connection with the present invention that the index m=1, 2, 3, as compounds can thus be provided, which can be used particularly well for curing epoxy resins or epoxy resin compositions, in particular as hardeners or cure accelerants. Without being bound to the theory, it may be said that the compulsorily present radical —NHC(O)NR$^1$R$^2$ exerts a decisive influence on the curing of epoxy resins. The radicals $R^1$ and $R^2$ in Formula (I) preferably mean here hydrogen or alkyl, wherein at least one radical $R^1$ or $R^2$ means not equal to hydrogen or the radicals $R^1$ and $R^2$ do not simultaneously mean hydrogen. Particularly preferably, the radicals $R^1$ and $R^2$, simultaneously or independently of one another, mean alkyl, wherein $R^1$ and $R^2$ may be different or the same. Most preferably the radicals $R^1$ and $R^2$ simultaneously mean methyl or ethyl.

The hardeners and cure accelerants according to the invention in tests for flame retardancy have been found to be particularly surprising compared to known hardeners and cure accelerants as flame-retarding hardeners and cure accelerants. These hardeners and cure accelerants are to be called halogen-free. Without being bound to the theory, it can be stated that these hardeners and cure accelerants have an additional effect as flame retardants compared to known hardeners or cure accelerants because of the phosphorus contained in the compounds. Thus, the hardeners and cure accelerants according to the invention have a good to very good effect as flame retardants in the cured epoxy resins.

Compared to currently used flame retardants for epoxy resins, which often have to be added in large quantities as an additive and are not chemically bound into the resin matrix, this is a reactive flame retardant, which is anchored directly in the resin matrix by a chemical bond. It is therefore not expected to be released from the matrix.

Therefore, the use of a compound according to Formula (I) or a hardener according to Formula (I) or a cure accelerant according to Formula (I) as a flame retardant in epoxy resins, or in powder paints, sealing compounds, adhesives or cured moulding compounds comprising, in each case, at least one epoxy resin, is also the subject of the present invention.

As already stated above, it has also been found that these compounds can be used as hardeners and/or as cure accelerants. Thus, it could be shown in experimental investigations that these compounds can be used as hardeners for curing epoxy resins, in particular as sole hardeners for curing epoxy resins.

According to an alternative embodiment, the compounds according to Formula (I) can also be used as cure accelerants for the accelerated curing of epoxy resins. In experimental investigations, it has been shown that the compounds according to the invention accelerate in particular the curing of epoxy resins, which are cured with dicyandiamide. Without being bound to the experimental results, the compounds according to the invention may, however, also be used as cure accelerants together with hardeners from the group of guanidine derivatives, aromatic amines, modified polyamines, semicarbazone derivatives or cyanamide. A curing can also be accelerated together with these hardeners.

Alternatively, or simultaneously, it may also be provided that a hardener or a cure accelerant according to the present invention is used together with a further hardener and/or cure accelerant according to Formula (I), which is different from the firstly mentioned hardener or cure accelerant of the present invention. Therefore, a hardener composition comprising or, in particular, consisting of at least two different hardeners and/or cure accelerants in each case according to Formula (I) is also the subject of the present invention. Therefore, a hardener composition comprising or, in particular, consisting of i) at least two different hardeners comprising, in each case, at least one compound from the group of esters of phosphorus-containing acids according to Formula (I) or according to Formula (Ia), or ii) at least two different cure accelerants comprising, in each case, at least one compound from the group of esters of phosphorus-containing acids according to Formula (I) or according to Formula (Ia), or iii) at least one hardener comprising at least one compound from the group of esters of phosphorus-containing acids according to Formula (I) or according to Formula (Ia), and at least one cure accelerant comprising at least one compound from the group of esters of phosphorus-containing acids according to Formula (I) or according to Formula (Ia), wherein the hardener and the cure accelerant are different from one another and comprise different compounds from the group of esters of phosphorus-containing acids according to Formula (I) or Formula (Ia), is also the subject of the present invention.

Alternatively, a hardener or a cure accelerant of the present invention can also be used together with known hardeners or accelerators. Therefore, a hardener composition comprising or, in particular, consisting of a) a hardener for curing epoxy resins, which is different from a hardener or cure accelerant according to Formula (I), or a cure accelerant for the accelerated curing of epoxy resins, which is different from a hardener or cure accelerant according to Formula (I) and b) at least one hardener or cure accelerant according to Formula (I), is also the subject of the present invention.

Particularly preferred is a hardener composition comprising or, in particular, consisting of a) at least one hardener for curing epoxy resins, which is different from a hardener and/or a cure accelerant comprising a compound from the group of esters of phosphorus-containing acids according to Formula (I) or Formula (Ia), and b) at least one cure accelerant for the accelerated curing of epoxy resins comprising a compound from the group of esters of phosphorus-containing acids according to Formula (I) or Formula (Ia).

In addition, it has furthermore been particularly surprisingly shown that the hardeners and cure accelerants according to the invention can not only be used particularly well for the curing or accelerated curing of epoxy resins, but they also have an excellent storage stability in epoxy resins. Therefore, the hardeners and cure accelerants can also be described as highly latent. The hardeners according to the invention can therefore also be provided as single-component pastes, i.e. preformulated, mixed ready for use with epoxy resin. These results were completely unexpected in total.

In a development of the present invention, epoxy resin compositions comprising a) at least one epoxy resin and b) at least one hardener according to the type described above and/or at least one cure accelerant according to the type described above are also the subject of the present invention.

The epoxy resin composition, apart from the hardener or cure accelerant, preferably comprises, in each case, according to Formula (I) or mixtures thereof a) no further hardener, co-hardener, cure accelerant or other catalysts for curing epoxy resins and/or b) no further flame-retardant additives or flame-retarding additives.

Therefore, an epoxy resin composition is also the subject of the present invention, which a) contains at least one epoxy resin and b) at least one hardener according to Formula (I) and/or at least one cure accelerant according to Formula (I), in particular consists thereof.

In a development of the present invention, in particular, epoxy resin compositions are therefore also the subject of the present invention, which comprise a) at least one epoxy resin, and b1) at least one hardener for curing epoxy resins comprising at least one compound from the group of esters of phosphorus-containing acids according to Formula (I) or Formula (Ia), and/or b2) at least one cure accelerant for the accelerated curing of epoxy resins comprising at least one compound from the group of esters of phosphorus-containing acids according to Formula (I) or Formula (Ia), wherein Formula (I) and Formula (Ia) have the structure described here.

However, it may also be provided that the epoxy resin composition according to the invention contains a) at least one epoxy resin, b) a cure accelerant according to Formula (I) and c) a hardener for curing epoxy resins, which is different from a hardener or cure accelerant according to Formula (I), in particular consists thereof.

However, it can also be provided that the epoxy resin composition according to the invention contains a) at least one epoxy resin, b) a cure accelerant for the accelerated curing of epoxy resins, which is different from a hardener or cure accelerant according to Formula (I), and c) a hardener for curing epoxy resins according to Formula (I), in particular consists thereof.

In a development of the present invention, in particular, epoxy resin compositions are therefore also the subject of the present invention, which comprise
   a) at least one epoxy resin, and
   b) at least one hardener for curing epoxy resins, which is different from a hardener and a cure accelerant comprising a compound from the group of esters of phosphorus-containing acids according to Formula (I) or Formula (Ia), and
   c) at least one cure accelerant for the accelerated curing of epoxy resins comprising a compound from the group of esters of phosphorus-containing acids according to Formula (I) or Formula (Ia),
wherein Formula (I) and Formula (Ia) have the structure described here.

In particular hardeners from the group of guanidine derivatives, in particular dicyandiamide, aromatic amines, modified polyamines, semicarbazone derivatives or cyanamide can be used here as component b).

With regard to the epoxy resins to be cured, the present invention is not subject to any limitation. All the conventional commercial products are possible that generally have more than one 1,2-epoxy group (oxirane) and can be saturated or unsaturated, aliphatic, cycloaliphatic, aromatic or heterocyclic here. Moreover, the epoxy resins may have substituents such as phosphorus and hydroxyl groups. Epoxy resins based on glycidyl polyether of 2,2-bis(4-hydroxyphenyl)-propane (bisphenol A), glycidyl polyether of 2,2-bis(4-hydroxyphenyl)methane (bisphenol F) and glycidyl polyether of novolacs can be cured particularly well by using the hardeners and cure accelerants according to the invention.

The application quantity of the hardeners or cure accelerants according to the invention is not subject to any limitations. However, 0.01 to 15 parts of hardener or cure accelerant, preferably 0.1 to 15 parts, preferably 0.1 to 10 parts and most preferably 0.1 to 8 parts, are preferably used for 100 parts resin. A combination of a plurality of hardeners according to the invention or a combination of hardeners according to the invention with further co-hardeners is also covered by this invention.

If a hardener according to the invention is to be used as the sole hardener, 0.1 to 15 parts, preferably 1 to 15 parts, preferably 4 to 15 parts and most preferably 4 to 8 parts are preferably used for 100 parts resin.

If a cure accelerator according to the invention is to be used for the accelerated curing together with a known hardener, such as, for example, dicyandiamide, 0.1 to 15 parts, preferably 0.1 to 10 parts, preferably 0.1 to 5 parts and most preferably 0.1 to 4 parts are preferably used for 100 parts resin.

The curing of the epoxy resins with the aid of the hardeners and/or cure accelerators used according to the invention generally takes place at temperatures from 20 to 140° C. The selection of the curing temperature depends on the specific processing and product requirement and may be varied by the formulation above all by regulating the hardener quantities and adding additives. It is unimportant here in what way energy is fed to the resin formulations. For example, this may take place in the form of heat by means of a furnace or heating elements, but also by means of infrared radiators or excitation by microwaves or other rays.

By adding further conventional commercial additives, as known to the person skilled in the art for curing epoxy resins, the curing profile of the formulations according to the invention can be varied.

Additives for improving the processability of the uncured epoxy resin compositions or for adapting the thermal-mechanical properties of the thermosetting products to the requirement profile comprise, for example, reactive diluting agents, fillers, rheology additives such as thixotropic agents or dispersing additives, defoamers, dyes, pigments, toughening agents or impact resistance improvers.

In a development of the invention, a prepreg or composite material is also the subject of the present invention, which comprises
   a) a carrier material, in particular a fibre material, and
   b) at least one epoxy resin, and
   c) at least one hardener or cure accelerant or a hardener composition of the type described here.

In a development of the invention, a prepreg or composite material is therefore, in particular, also the subject of the present invention, which comprises
   a) a carrier material, in particular a fibre material, and
   b) at least one epoxy resin, and
   c1) at least one hardener for curing epoxy resins, which is different from a hardener and a cure accelerant comprising a compound from the group of esters of phosphorus-containing acids according to Formula (I) or Formula (Ia), and
   c2) at least one cure accelerant for the accelerated curing of epoxy resins comprising a compound from the group of esters of phosphorus-containing acids according to Formula (I) or Formula (Ia),
wherein Formula (I) and Formula (Ia) have the structure described here.

All conventional carrier materials may be used as the carrier material here. To be mentioned here, in particular, but not conclusively are: fibres made of glass, carbon, aramid and wood or natural fibres.

In a development of the invention, a method for producing the compounds described here is also the subject of the present invention. Therefore, a method for producing a compound of Formula (I), in particular a compound selected from the group of phosphoric acid esters, thiophosphoric acid esters, phosphonates, thiophosphonates, phosphinates and thiophosphinates according to Formula (I), is therefore also the subject of the present invention, wherein there applies to Formula (I):

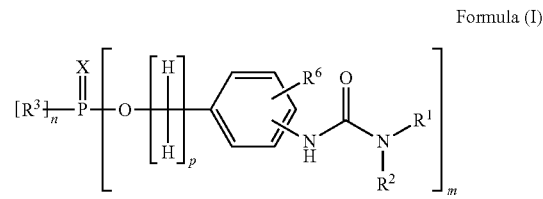

Formula (I)

wherein there applies to the radicals $R^1$, $R^2$, $R^3$, $R^6$, X and indices m, n, p, simultaneously or independently of one another:

$R^1$, $R^2$=simultaneously or independently of one another, hydrogen or alkyl, in particular simultaneously or independently of one another, methyl or ethyl, $R^3$=alkyl, aryl, —O-alkyl, —O-aryl, —O-alkylaryl or —O-arylalkyl, in particular phenyl, phenoxy or tolyloxy, $R^6$=hydrogen, alkyl or —NHC(O)NR$^1$R$^2$, in particular hydrogen or alkyl, particularly preferably hydrogen or methyl, X=oxygen or sulphur,
m=1, 2 or 3,
n=0, 1 or 2, wherein there applies: m+n=3
p=0, 1 or 2, in particular 0,
comprising the method steps:
A) providing a compound according to Formula (II),

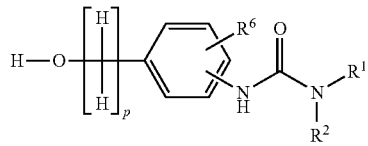

Formula (II)

wherein for the radicals $R^1$, $R^2$, $R^6$ and the index p, the meaning given above applies,
B) reacting the compound provided in A) with a compound according to Formula (III),

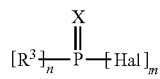

Formula (III)

wherein for the radicals $R^3$, X and the indices m, n the meaning given above applies, and Hal=chlorine or bromine, in particular chlorine,
C) isolating the compound according to Formula (I).

It has been found in laborious experimental investigations that the desired compounds according to Formula (I) proceeding from the compounds according to Formula (II) and Formula (III) can be shown having a good space-time yield. It has particularly surprisingly been found that the desired compounds can be shown selectively.

A compound according to Formula (II) is preferably provided here in method step A), wherein there applies to the radicals $R^1$, $R^2$, $R^6$ and the index p, simultaneously or independently of one another:
$R^1$, $R^2$=simultaneously or independently of one another, alkyl, in particular simultaneously alkyl, in particular, simultaneously or independently of one another, methyl or ethyl, in particular simultaneously methyl or ethyl,
$R^6$=hydrogen, alkyl or —NHC(O)NR$^1$R$^2$, in particular hydrogen or alkyl, particularly preferably hydrogen or methyl,
p=0.

Therefore, a method is also the subject of the present invention, in which in method step A) a compound according to Formula (IIa) is provided and this compound is reacted according to Formula (IIa) in method step B), as described above, wherein there applies to Formula (IIa):

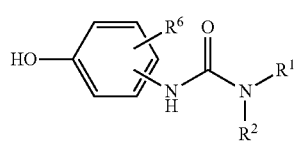

Formula (IIa)

wherein there applies to the radicals $R^1$, $R^2$, $R^6$, simultaneously or independently of one another:

$R^1$, $R^2$=simultaneously or independently of one another, alkyl, in particular simultaneously alkyl, in particular, simultaneously or independently of one another, methyl or ethyl, in particular simultaneously methyl or ethyl,
$R^6$=hydrogen, alkyl or —NHC(O)NR$^1$R$^2$, in particular hydrogen or alkyl, particularly preferably hydrogen or methyl.

Compounds according to Formula (II) or Formula (IIa) are used here, which can in turn be produced according to methods known from the literature (cf. in this regard, in particular GB 999 862 A, GB 1 153 261 A, U.S. Pat. Nos. 3,488,376 A, 2,795,610 A and EP 0 108 712 A1).

In additional experimental investigations, it has further been advantageously found that the reaction in method step B) can be carried out particularly successfully in a polar-aprotic solvent, in particular acetonitrile, N,N-dimethylformamide and/or acetone, preferably acetonitrile. Simultaneously or independently thereof, it may furthermore be provided here that the reaction takes place in the presence of a tertiary amine, in particular triethylamine, tri-n-butylamine, triisopropylamine and/or pyridine, preferably triethylamine.

The reaction can preferably be carried out here at a temperature in the range from −10 to 100° C., in particular at a temperature in the range from −10 to 80° C., most preferably at a temperature in the range from −10 to 60° C., wherein, simultaneously or independently thereof, in particular a pressure in the range from 850 to 1,200 mPa, in particular a pressure in the range from 950 to 1,200 mPa, and most preferably a pressure in the range from 1,000 to 1,200 mPa is adjusted.

More preferably, the reaction can be carried out in method step B) when the molar ratio of the compound according to Formula (II) or Formula (IIa) to the compound according to Formula (III), corresponds to a ratio in the range from 4:1 to 1:1, preferably 3:1 to 1:1, more preferably 3:1 to 2:1.

Experimental investigations have furthermore shown that isolating the compound according to Formula (I) in method step C) can take place according to different method substeps. The compounds according to the invention can be isolated particularly advantageously and in good purities by a) filtering them off from the reaction mixture from method step B), subsequent washing with water and drying in a vacuum, or b) precipitation from the reaction mixture from method step B) by adding water, filtering off the solid that has been produced, subsequent washing with water and drying in a vacuum, or c) vaporising the reaction mixture from method step B) in a vacuum, absorbing the residue in acetone, filtering off the insoluble components, vaporising the filtrate in a vacuum and drying in a vacuum.

Alternatively, the desired compounds according to Formula (I) can also be shown by the reaction of isocyanates with amines. Thus, a method for producing a compound of Formula (I), in particular a compound selected from the group of phosphoric acid esters, thiophosphoric acid esters, phosphonates, thiophosphonates, phosphinates and thiophosphinates according to Formula (I), is also the subject of the present invention, wherein there applies to Formula (I):

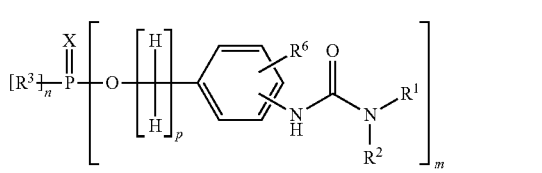

Formula (I)

wherein there applies to the radicals $R^1$, $R^2$, $R^3$, $R^6$, X and indices m, n, p, simultaneously or independently of one another:
  $R^1$, $R^2$=simultaneously or independently of one another, hydrogen or alkyl, in particular simultaneously or independently of one another, methyl or ethyl,
  $R^3$=alkyl, aryl, —O-aryl, —O-alkylaryl or —O-arylalkyl, in particular phenyl, phenoxy or tolyloxy,
  $R^6$=hydrogen, alkyl or —NHC(O)N$R^1R^2$, in particular hydrogen or alkyl, particularly preferably hydrogen or methyl,
  X=oxygen or sulphur,
  m=1, 2 or 3,
  n=0, 1 or 2, wherein there applies: m+n=3
  p=0, 1 or 2, in particular 0,
comprising the method steps:
A) providing an isocyanate according to Formula (IV),

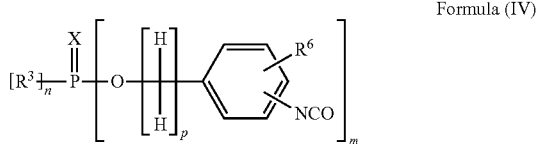

Formula (IV)

wherein there applies to the radicals $R^3$, $R^6$, X and indices m, n, p, simultaneously or independently of one another:
  $R^3$=alkyl, aryl, —O-aryl, —O-alkylaryl or —O-arylalkyl, in particular phenyl, phenoxy or tolyloxy,
  $R^6$=hydrogen, alkyl or —NCO, in particular hydrogen or alkyl, particularly preferably hydrogen or methyl,
  X=oxygen or sulphur,
  m=1, 2 or 3,
  n=0, 1 or 2, wherein there applies: m+n=3
  p=0, 1 or 2.
B) reacting the compound provided in A) with an amine according to Formula (V),

Formula (V)

wherein there applies to the radicals $R^1$, $R^2$, simultaneously or independently of one another:
  $R^1$, $R^2$=simultaneously or independently of one another, hydrogen or alkyl, in particular simultaneously or independently of one another, alkyl, in particular, simultaneously or independently of one another, methyl or ethyl, in particular simultaneously methyl or ethyl,
C) isolating the compound according to Formula (I).

A compound according to Formula (IV) is preferably provided here in method step A), wherein there applies to the radicals $R^3$, $R^6$, X and the indices m, n, p, simultaneously or independently of one another:
  $R^3$=alkyl, aryl, —O-aryl, —O-alkylaryl or —O-arylalkyl,
  $R^6$=hydrogen, alkyl or —NCO, in particular hydrogen or alkyl, particularly preferably hydrogen or methyl,
  X=oxygen or sulphur,
  m=1, 2 or 3,
  n=0, 1 or 2, wherein there applies: m+n=3
  p=0.
Therefore, a method is also the subject of the present invention, in which in method step A) a compound according to Formula (IVa) is provided and this compound is reacted according to Formula (IVa) in method step B), as described above, wherein there applies to Formula (IVa):

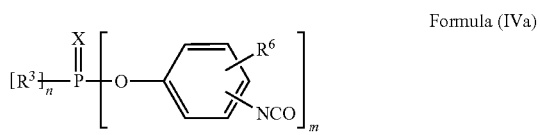

Formula (IVa)

wherein there applies to the radicals $R^3$, $R^6$, X and the indices m, n, simultaneously or independently of one another:
  $R^3$=alkyl, aryl, —O-aryl, —O-alkylaryl or —O-arylalkyl,
  $R^6$=hydrogen, alkyl or —NCO, in particular hydrogen or alkyl, particularly preferably hydrogen or methyl,
  X=oxygen or sulphur,
  m=1, 2 or 3,
  n=0, 1 or 2, where: m+n=3.

A solvent or a solvent mixture selected from the group of a) polar-aprotic solvents, in particular ethyl acetate, acetonitrile, N,N-dimethylformamide or acetone, preferably ethyl acetate or b) nonpolar-aprotic solvents, in particular toluene, cyclohexane or n-hexane, preferably toluene, or c) a solvent mixture consisting of a solvent from a) and a solvent from b), in particular a mixture of ethyl acetate and toluene, can particularly preferably be implemented here as the solvent.

The reaction can more preferably be carried out here at a temperature in the range from −10 to 100° C., in particular at a temperature in the range from −10 to 80° C., most preferably at a temperature in the range from 0 to 60° C., wherein, simultaneously or independently thereof, in particular a pressure in the range from 850 to 1,200 mPa, in particular a pressure in the range from 950 to 1,200 mPa, and most preferably a pressure in the range from 1,000 to 1,200 mPa is adjusted.

More preferably, the reaction in method step B) can be carried out with particularly good results when the molar ratio of the compound according to Formula (IV) to the compound according to Formula (V) corresponds to a ratio in the range from 1:6 to 1:1, preferably 5:1 to 1:1, preferably 4:1 to 1:1, preferably 3:1 to 1:1.

According to a development of the invention, the use of a compound described here according to Formula (I) or Formula (Ia) for curing epoxy resins or epoxy resin compositions is also the subject of the present invention. Therefore, the use of a hardener and a cure accelerant comprising, in each case, at least one compound selected from the group of esters of phosphorus-containing acids according to Formula (I) or Formula (Ia) as
  a) a hardener for curing prepregs, laminates, coatings, polymer resin mixtures, powder paints, sealing compounds or adhesives, in each case comprising at least one epoxy resin, and/or b) a cure accelerant for the accelerated curing of prepregs, laminates, coatings, polymer resin mixtures, powder paints, sealing compounds or adhesives, in each case comprising at least one epoxy resin, or c) a flame retardant in epoxy resins, or in powder paints, sealing compounds, adhesives or cured moulding compounds comprising in each case at least one epoxy resin, is also the subject of the invention.

The present invention will be described below with the aid of examples, wherein the invention is not to be understood to be reduced to the examples, however. It is rather the case that each combination of preferred embodiments is also comprised by the present invention.

EXAMPLES

1) Substances Used and Associated Abbreviations

Epoxy Resin:
ER epoxy resin with EEW 182-187 (Epikote® Resin 828 LVEL, Hexion)
Hardeners/Cure Accelerants:
HA TDI-Uron (DYHARD® UR500, AlzChem AG)
H dicyandiamide (DYHARD® 100S, AlzChem AG)
HA-I tri[p-(dimethylcarbamoylamino)phenyl]thiophosphate
HA-II tri[p-(diethylcarbamoylamino)phenyl]thiophosphate
HA-III tri[p-(dimethylcarbamoylamino)phenyl]phosphate
HA-IV di[p-(dimethylcarbamoylamino)phenyl]phenyl phosphate
HA-V [p-dimethylcarbamoylamino)phenyl]diphenyl phosphate
HA-VI di[p-(dimethylcarbamoylamino)phenyl]phenyl phosphonate
HA-VII [p-dimethylcarbamoylamino)phenyl]diphenylphosphinate
HA-VI II tri[m-(dimethylcarbamoylamino)phenyl]phosphate
HA-IX tri[o-(dimethylcarbamoylamino)phenyl]phosphate
HA-X tri[4-(dimethylcarbamoylamino)-3-methylphenyl]phosphate

2) Production of the Hardeners/Cure Accelerants According to the Invention

Example 1: tri[p-(dimethylcarbamoylamino)phenyl]thiophosphate (HA-I)

HA-I corresponds to a compound according to Formula (I) with m=3; p=0; X=S; $R^1=R^2$=methyl; $R^6$=H, wherein the —NHC(O)$NR^1R^2$ group is in the p-position.

A solution of 12.17 g (0.27 mol) dimethylamine (99%, Linde) in 400 ml toluene is prepared (for analysis, Merck) in an $N_2$-washed three-necked flask with a return condenser, dropping funnel, thermometer and magnetic stirrer. A solution of 27.92 g (60 mmol) tri(p-isocyanatophenyl)thiophosphate (27% in ethyl acetate, Bayer MaterialScience) in 285 ml toluene is slowly added drop-wise by means of the dropping funnel, so the temperature does not rise above 25° C. (optionally cooling by water bath). During the addition, white solid precipitates. Once the addition has ended, the suspension produced is still stirred for 1.5 h at room temperature. The solid is separated off, washed with a little toluene and dried at 60° C. in a vacuum.

Yield: 36.00 g (100%)

Elementary analysis: prov.: 53.99% C; 5.54% H; 13.99% N; 5.16% P found: 54.14% C; 5.68% H; 13.70% N; 5.22% P.

IR: $\tilde{v}$ ($cm^{-1}$)=3356 (w); 1647 (s); 1605 (m); 1533 (m); 1501 (vs); 1407 (s); 1370 (s); 1303 (m); 1246 (m); 1179 (vs); 1159 (vs); 928 (vs); 832 (s); 779 (s); 754 (s); 580 (w); 558 (w); 521 (s)

$^1$H-NMR (500.13 MHz, DMSO-$d_3$): δ (ppm)=2.91 (s, 18H, $CH_3$); 7.12 (d, 6H, Ar—H, $^3J_{HH}$=8.0 Hz); 7.50 (d, 6H, Ar—H, $^3J_{HH}$=9.0 Hz); 8.37 (s, 3H, NH)

$^{13}$C-NMR (125.77 MHz, DMSO-$d_6$): δ (ppm)=36.20 ($CH_3$); 120.63 (d, Ar—C, $^3J_{PC}$=4.6 Hz); 120.88 (Ar—C); 138.51 (Ar—C); 144.46 (d, Ar—C, $^2J_{PC}$=8.3 Hz); 155.68 (C=O)

$^{31}$P-NMR (202.46 MHz, DMSO-$d_6$): δ (ppm)=55.08 (S=P(OAr)$_3$)

Example 2: tri[p-(diethylcarbamoylamino)phenyl]thiophosphate (HA-II)

HA-II corresponds to a compound according to Formula (i) with m=3; n=p=0; X=S; $R^1=R^2$=ethyl; $R^6$=H, wherein the —NHC(O)$NR^1R^2$ group is in the p-position.

The production of HA-II takes place analogously to example 1, wherein dimethylamine is replaced by 19.75 g (0.27 mol) diethylamine (99%, Fluka).

Yield: 40.20 g (98%)

Elementary analysis: prov.: 57.88% C; 6.62% H; 12.27% N; 4.52% P found: 57.75% C; 6.48% H; 12.15% N; 4.42% P.

IR: $\tilde{v}$ ($cm^{-1}$)=3291 (w); 2973 (w); 2931 (w); 1632 (s); 1603 (m); 1502 (vs); 1450 (m); 1418 (s); 1379 (m); 1303 (m); 1267 (m); 1249 (m); 1223 (vs); 1159 (vs); 1100 (m); 1080 (m); 941 (vs); 920 (vs); 830 (s); 779 (m); 752 (m)

$^1$H-NMR (500.13 MHz, DMSO-$d_6$): δ (ppm)=1.08 (t, 18H, $CH_3$, $^3J_{HH}$=7.0 Hz); 3.33 (q, 12H, $CH_2$, $^3J_{HH}$=7.1 Hz); 7.12 (d, 6H, Ar—H, $^3J_{HH}$=8.0 Hz); 7.52 (d, 6H, Ar—H, $^3J_{HH}$=9.1 Hz); 8.24 (s, 3H, NH)

$^{13}$C-NMR (125.77 MHz, DMSO-$d_6$): δ (ppm)=13.86 ($CH_3$); 40.52 ($CH_2$); 120.54 (d, Ar—C, $^3J_{PC}$=3.7 Hz); 121.13 (Ar—C); 138.51 (Ar—C); 144.46 (d, Ar—C, $^2J_{PC}$=8.2 Hz); 154.35 (C=O)

$^{31}$P-NMR (202.46 MHz, DMSO-$d_6$): δ (ppm)=55.14 (S=P(OAr)$_3$)

Example 3: tri[p-(dimethylcarbamoylamino)phenyl]phosphate (HA-III)

HA-III corresponds to a compound according to Formula (I) with m=3; p=0; X=O; $R^1=R^2$=methyl; $R^6$=H, wherein the —NHC(O)$NR^1R^2$ group is in the p-position.

a) Production of N-(p-hydroxyphenyl)-N',N'-dimethylurea

The production of N-(p-hydroxyphenyl)-N',N'-dimethylurea takes place as described in the patent EP 0 108 712 A1, using 90.00 g (0.825 mol) p-aminophenol (98%, TCI), 90.00 g (0.837 mol) N, N-dimethylcarbamoylchloride (98%, Aldrich), 84.00 g (1,000 mol) sodium bicarbonate (for the analysis, Merck) and 1,800 ml acetone (99.8%, VWR, dried by molecular sieve).

Yield: 82.48 g (55%)

Elementary analysis: prov.: 59.99% C; 6.71% H; 15.55% N found: 59.90% C; 6.71% H; 15.50% N.

Melting point: 204° C. (DSC-Onset), 210° C. (DSC-Peak)
IR: ṽ (cm$^{-1}$)=3341 (w); 3181 (w); 2929 (w); 1615 (m); 1594 (m); 1505 (vs); 1485 (s); 1372 (vs); 1300 (m); 1271 (vs); 1189 (s); 1163 (s); 1103 (m); 1066 (m); 844 (m); 820 (s); 748 (s); 562 (s); 514 (s)

b) Production of HA-III 3.78 g (21 mmol) N-(p-hydroxyphenyl)-N',N'-dimethylurea in 20 ml acetonitrile (100%, VWR) are prepared in an N$_2$-washed three-necked flask with a return condenser, dropping funnel, thermometer and magnetic stirrer, 2.13 g (21 mmol) triethylamine (99.5%, Sigma-Aldrich) are added and the reaction mixture being produced is cooled by means of an ice bath to a temperature of 0° C. A solution of 1.07 g (7 mmol) phosphoryl chloride (for synthesis, Merck) in 10 ml acetonitrile is added drop-wise by means of a dropping funnel in such a way that the temperature does not rise above 5° C. Thereafter, the ice bath is removed and the reaction mixture is stirred overnight at room temperature. The reaction mixture is diluted with 250 ml water. The solid precipitating thereafter is separated off, rewashed with a little water and dried at 60° C.

Yield: 3.49 g (85%)

Elementary analysis: prov.: 55.48% C; 5.69% H; 14.38% N; 5.300% P found: 55.19% C; 567% H; 14.26% N; 524% P.

Melting point: 174.5° C. (DSC-Onset), 180.5° C. (DSC-Peak)
IR: ṽ (cm$^{-1}$)=3352 (w); 2924 (w); 1650 (m); 1605 (w); 1532 (m); 1500 (vs); 1409 (s); 1366 (s); 1301 (w); 1280 (m); 1244 (w); 1218 (w); 1160 (vs); 1108 (w); 1067 (w); 1015 (w); 989 (s); 964 (vs); 930 (s); 884 (w); 832 (s); 752 (m); 583 (m)

$^1$H-NMR (500.13 MHz, DMSO-d$_6$): δ (ppm)=2.91 (s, 18H, CH$_3$); 7.11 (d, 6H, Ar—H, $^3J_{HH}$=8.7 Hz); 7.49 (d, 6H, Ar—H, $^3J_{HH}$=9.0 Hz); 8.37 (s, 3H, NH)

$^{13}$C-NMR (125.77 MHz, DMSO-d$_6$): δ (ppm)=36.20 (CH$_3$); 119.70 (d, Ar—C, $^3J_{PC}$=4.6 Hz); 120.98 (Ar—C); 138.41 (Ar—C); 144.29 (d, Ar—C, $^2J_{PC}$=7.3 Hz); 155.70 (C=O)

$^{31}$P-NMR (202.46 MHz, DMSO-d$_6$): δ (ppm)=−15.94 (O=P(OAr)$_3$)

Example 4: di[p-(dimethylcarbamoylamino)phenyl] phenyl phosphate (HA-IV)

HA-IV corresponds to a compound according to Formula (I) with m=2; n=1; p=0; X=O; R$^1$=R$^2$=methyl; R$^3$=—O-phenyl; R$^6$=H, wherein the —NHC(O)NR$^1$R$^2$ group is in the p-position.

28.83 g (160 mmol) N-(p-hydroxyphenyl)-N',N'-dimethylurea are suspended in 160 ml acetonitrile (100%, VWR) in an N$_2$-washed three-necked flask with a return condenser, dropping funnel, thermometer and magnetic stirrer, 16.19 g (160 mmol) triethylamine (99.5%, Sigma-Aldrich) are added and the mixture being produced is cooled by means of an ice bath to a temperature of 0° C. A solution of 16.88 g (80 mmol) phosphoric acid phenyl ester dichloride (97%, ABCR) in 80 ml acetonitrile is added drop-wise by means of a dropping funnel in such a way that the temperature does not rise above 5° C. Thereafter, the ice bath is removed and the reaction mixture is stirred overnight at room temperature. The solid produced is separated off, rewashed with a little acetonitrile and dried in air. The solid is then suspended in 200 ml water, stirred at 50° C. for 30 min, separated off again and rewashed again with water. Drying then takes place at 60° C. in a vacuum.

Yield: 34.95 g (88%)

Elementary analysis: prov.: 57.83% C; 5.46% H; 11.24% N; 6.21% P found: 57.79% C; 5.49% H; 11.39% N; 6.11% P.

Melting point: 204° C. (DSC-Onset), 208.5° C. (DSC-Peak)
IR: ṽ (cm$^{-1}$)=3310 (w); 1656 (s); 1601 (w); 1531 (s); 1505 (s); 1488 (s); 1410 (m); 1374 (m); 1299 (s); 1246 (w); 1221 (w); 1181 (vs); 1161 (s); 1106 (w); 1075 (w); 1027 (w); 1011 (w); 975 (s); 956 (vs); 936 (m); 892 (w); 830 (s); 756 (s); 523 (s)

$^1$H-NMR (500.13 MHz, DMSO-d$_6$): δ (ppm)=2.91 (s, 12H, CH$_3$); 7.12 (m, 4H, Ar—H); 7.23-7.30 (m, 3H, Ar—H); 7.44 (t, 2H, Ar—H, $^3J_{HH}$=8.0 Hz); 7.49 (d, 4H, Ar—H, $^3J_{HH}$=9.0 Hz); 8.37 (s, 2H, NH)

$^{13}$C-NMR (125.77 MHz, DMSO-d$_6$): δ (ppm)=36.20 (CH$_3$); 119.67 (d, Ar—C, $^3J_{PC}$=4.6 Hz); 119.92 (d, Ar—C, $^3J_{PC}$=4.6 Hz); 120.95 (Ar—C); 125.78 (Ar—C); 130.19 (Ar—C); 138.46 (Ar—C); 144.17 (d, Ar—C, $^2J_{PC}$=8.3 Hz); 149.99 (d, Ar—C, $^2J_{PC}$=7.3 Hz); 155.66 (C=O)

$^{31}$P-NMR (202.46 MHz, DMSO-d$_6$): δ (ppm)=−16.35 (O=P(OAr)$_3$)

Example 5: [p-(dimethylcarbamoylamino)phenyl] diphenyl phosphate (HA-V)

HA-V corresponds to a compound according to Formula (I) with m=1; n=2; p=0; X=O; R$^1$=R$^2$=methyl; R$^3$=—O-phenyl; R$^6$=H, wherein the —NHC(O)NR$^1$R$^2$ group is in the p-position.

28.83 g (160 mmol) N-(p-hydroxyphenyl)-N',N'-dimethylurea are suspended in 160 ml acetonitrile (100%, VWR) in an N$_2$-washed three-necked flask with a return condenser, dropping funnel, thermometer and magnetic stirrer, 16.19 g (160 mmol) triethylamine (99.5%, Sigma-Aldrich) are added and the mixture being produced is cooled by means of an ice bath to a temperature of 0° C. A solution of 42.98 g (160 mmol) phosphoric acid diphenyl ester chloride (97%, ABCR) in 80 ml acetonitrile is added drop-wise by means of a dropping funnel in such a way that the temperature does not rise above 5° C. After the removal of the ice bath, the mixture is stirred for 90 min at room temperature and thereafter stirred again for 90 min at a temperature of 50° C. After cooling to room temperature, 400 ml water are added, a two-phase mixture being produced. The upper, aqueous phase is separated off and 240 ml water added to the organic phase. The solid being produced here is separated off, washed with water and dried at 60° C. in a vacuum.

Yield: 56.93 g (86%)

Elementary analysis: prov.: 61.16% C; 5.13% H; 6.79% N; 7.51% P found: 61.12% C; 5.09% H; 6.93% N; 7.38% P.

Melting point: 91° C. (DSC-Onset), 94° C. (DSC-Peak)
IR: ṽ (cm$^{-1}$)=3258 (w); 2930 (w); 1639 (s); 1588 (w); 1543 (m); 1507 (s); 1485 (s); 1455 (m); 1415 (m); 1377 (m); 1311 (s); 1302 (s); 1223 (w); 1183 (vs); 1157 (vs); 1068 (w); 1024 (m); 1017 (m); 1008 (m); 976 (s); 949 (vs); 927 (vs); 902 (s); 828 (s); 768 (s); 750 (s); 684 (s); 513 (vs)

$^1$H-NMR (500.13 MHz, DMSO-d$_6$): δ (ppm)=2.91 (s, 6H, CH$_3$); 7.14 (m, 2H, Ar—H); 7.23-7.31 (m, 6H, Ar—H); 7.44 (t, 4H, Ar—H, $^3J_{HH}$=7.7 Hz); 7.50 (d, 2H, Ar—H, $^3J_{HH}$=9.0 Hz); 8.38 (s, 1H, NH)

$^{13}$C-NMR (125.77 MHz, DMSO-d$_6$): δ (ppm)=36.17 (CH$_3$); 119.69 (d, Ar—C, $^3J_{PC}$=4.6 Hz); 119.91 (d, Ar —C, $^3J_{PC}$=4.6 Hz); 120.97 (Ar—C); 125.84 (Ar—C); 130.20 (Ar—C); 138.56 (Ar—C); 144.12 (d, Ar—C, $^2J_{PC}$=7.3 Hz); 149.93 (d, Ar—C, $^2J_{PC}$=7.3 Hz); 155.67 (C=O)

$^{31}$P-NMR (202.46 MHz, DMSO-d$_6$): δ (ppm)=−16.74 (O=P(OAr)$_3$)

Example 6: di[p-(dimethylcarbamoylamino)phenyl] phenyl phosphonate (HA-VI)

HA-VI corresponds to a compound according to Formula (I) with m=2; n=1; p=0; X=O; R$^1$=R$^2$=methyl; R$^3$=phenyl; R$^6$=H, wherein the —NHC(O)NR$^1$R$^2$ group is in the p-position.

3.60 g (20 mmol) N-(p-hydroxyphenyl)-N''N'-dimethylurea in 20 ml acetonitrile (100%, VWR) are prepared in an N$_2$-washed three-necked flask with a return condenser, dropping funnel, thermometer and magnetic stirrer, 2.02 g (20 mmol) triethylamine (99.5%, Sigma-Aldrich) are added and the reaction mixture being produced is cooled by means of an ice bath to a temperature of 0° C. A solution of 1.95 g (10 mmol) phenylphosphonic acid dichloride (for synthesis, Merck) in 10 ml acetonitrile is added drop-wise by means of a dropping funnel in such a way that the temperature does not rise above 5° C. Thereafter, the ice bath is removed and the reaction mixture is stirred overnight at room temperature. The reaction mixture is diluted with 150 ml water. The solid being precipitated is separated off, rewashed with a little water and dried at 60° C. in a vacuum.

Yield: 3.91 g (81%)

Elementary analysis: prov.: 59.75% C; 5.64% H; 11.61% N; 6.42% P found: 59.31% C; 5.70% H; 11.49% N; 6.36% P.

Melting point: 195° C. (DSC-Onset), 200° C. (DSC-Peak)

IR: ṽ (cm$^{-1}$)=3266 (w); 2923 (w); 1652 (s); 1603 (w); 1532 (s); 1504 (s); 1440 (m); 1410 (m); 1372 (m); 1305 (m); 1266 (m), 1184 (vs); 1162 (s); 1069 (w); 1015 (w); 939 (s); 918 (vs); 891 (m); 854 (m); 828 (vs); 756 (s); 559 (s); 519 (vs)

$^1$H-NMR (500.13 MHz, DMSO-d$_6$): δ (ppm)=2.89 (s, 12H, CH$_3$); 7.03 (m, 4H, Ar—H); 7.36-7.44 (m, 4H, Ar—H); 7.53-7.61 (m, 2H, Ar—H); 7.65-7.71 (m, 1H, Ar—H); 7.83-7.93 (m, 2H, Ar—H); 8.29 (s, 2H, NH)

$^{13}$C-NMR (125.77 MHz, DMSO-d$_6$): δ (ppm)=36.17 (CH$_3$); 120.12 (d, O—Ar—C, $^3J_{PC}$=3.7 Hz); 120.92 (O—Ar—C); 126.32 (d, P—Ar—C, $^3J_{PC}$=188.8 Hz); 128.96 (d, P—Ar—C, $^3J_{PC}$=15.6 Hz); 132.07 (d, P—Ar—C, $^2J_{PC}$=10.1 Hz): 133.50 (d, P—Ar—C, $^4J_{PC}$=2.8 Hz); 137.93 (O—Ar—C); 144.16 (d, O—Ar—C, $^2J_{PC}$=7.3 Hz); 155.67 (C=O)

$^{31}$P-NMR (202.46 MHz, DMSO-d$_6$): δ (ppm)=12.31 (t, O=P(Ar)(OAr)$_2$, $^3J_{PH}$=13.2 Hz)

Example 7: [(p-(dimethylcarbamoylamino)phenyl] diphenyl phosphinate (HA-VII)

HA-VII corresponds to a compound according to Formula (I) with m=1; n=2; p=0; X=O; R$^1$=R$^2$=methyl; R$^3$=phenyl; R$^6$=H, wherein the —NHC(O)NR$^1$R$^2$ group is in the p-position.

3.60 g (20 mmol) N-(p-hydroxyphenyl)-N',N'-dimethylurea in 20 ml acetonitrile (100%, VWR) are prepared in an N$_2$-washed three-necked flask with a return condenser, dropping funnel, thermometer and magnetic stirrer, 2.02 g (20 mmol) triethylamine (99.5%, Sigma-Aldrich) are added and the reaction mixture being produced is cooled by means of an ice bath to a temperature of 0° C. A solution of 4.72 g (20 mmol) diphenylphosphinic acid chloride (98%, Acros Organics) in 10 ml acetonitrile is added drop-wise by means of a dropping funnel in such a way that the temperature does not rise above 5° C. Thereafter, the ice bath is removed and the reaction mixture is stirred overnight at room temperature. The reaction mixture is diluted with 50 ml water. The solid being precipitated is separated off, rewashed with a little water and dried at 60° C. in a vacuum.

Yield: 6.35 g (83%)

Elementary analysis: prov.: 66.31% C; 5.56% H; 7.36% N; 8.14% P found: 66.30% C; 5.50% H; 7.43% N; 8.26% P.

Melting point: 222° C. (DSC-Onset), 223.5° C. (DSC-Peak)

IR: ṽ (cm$^{-1}$)=3312 (w); 3061 (w); 2921 (w); 1658 (s); 1601 (w); 1532 (m); 1505 (s); 1484 (m); 1439 (m); 1410 (m); 1370 (m); 1305 (w); 1293 (w); 1229 (s); 1190 (s); 1166 (s); 1128 (s); 1112 (s); 1072 (w); 1017 (w); 996 (w); 955 (w); 922 (vs); 839 (s); 817 (w); 725 (vs); 687 (s); 585 (vs); 538 (s); 527 (vs)

$^1$H-NMR (500.13 MHz, DMSO-d$_6$): δ (ppm)=2.87 (s, 6H, CH$_3$); 7.09-7.13 (m, 2H, Ar—H); 7.30-7.38 (m, 2H, Ar—H); 7.49-7.56 (m, 4H, Ar—H); 7.56-7.64 (m, 2H, Ar—H); 7.82-7.93 (m, 4H, Ar—H); 8.22 (s, 1H, NH)

$^{13}$C-NMR (125.77 MHz, DMSO-d$_6$): δ (ppm)=36.14 (CH$_3$); 120.30 (d, O—Ar—C, $^3J_{PC}$=4.6 Hz); 120.89 (O—Ar—C); 128.83 (d, P—Ar—C, $^3J_{PC}$=12.8 Hz); 130.89 (d, P—Ar—C, $^1J_{PC}$=136.6 Hz); 131.52 (d, P—Ar—C, $^2J_{PC}$=10.1 Hz); 132.61 (d, P—Ar—C, $^4J_{PC}$=2.8 Hz); 137.38 (O—Ar—C); 144.95 (d, O—Ar—C, $^2J_{PC}$=8.3 Hz); 155.67 (C=O)

$^{31}$P-NMR (202.46 MHz, DMSO-d$_6$): δ (ppm)=29.01 (t, O=P(Ar)$_2$(OAr), $^3J_{PH}$=11.7 Hz)

Example 8: tri[m-(dimethylcarbamoylamino)phenyl] phosphate (HA-VIII)

HA-VIII corresponds to a compound according to Formula (I) with m=3; n=p=0; X=O; R$^1$=R$^2$=methyl; R$^6$=H, wherein the —NHC(O)NR$^1$R$^2$ group is in the m-position.

a) Production of N-(m-hydroxyphenyl)-N',N'-dimethylurea

The production of N-(m-hydroxyphenyl)-N',N'-dimethylurea takes place as described in patent EP 0 108 712 A1, using 50.00 g (0.458 mol) m-aminophenol (99%, Merck), 37.10 g (0.345 mol) N, N-dimethylcarbamoylchloride (98%, Aldrich) and 325 ml tetrahydrofuran (99.8%, Merck).

Yield: 34.67 g (56%)

Elementary analysis: prov.: 59.99% C; 6.71% H; 15.55% N found: 59.92% C; 6.67% H; 15.37% N.

Melting point: 193° C. (DSC-Onset), 196.5° C. (DSC-Peak)

IR: ṽ (cm)=3369 (w); 3088 (w); 1633 (m); 1602 (m); 1537 (s); 1484 (s); 1437 (vs); 1376 (s); 1270 (s); 1231 (m); 1203 (vs); 1168 (s): 1157 (s); 1065 (m); 1031 (w); 972 (m); 871 (m); 853 (m); 777 (s); 765 (s); 740 (s); 692 (s); 610 (s)

b) Production of HA-VIII 8.11 g (45 mmol) N-(m-hydroxyphenyl)-N',N'-dimethylurea in 50 ml acetonitrile (100%, VWR) are prepared in an N$_2$-washed three-necked flask with a return condenser, dropping funnel, thermometer and magnetic stirrer, 4.55 g (45 mmol) triethylamine (99.5%, Sigma-Aldrich) are added and the reaction mixture being produced is cooled by means of an ice bath to a temperature of 0° C. A solution of 2.30 g (15 mmol) phosphoryl chloride (for synthesis, Merck) in 25 ml acetonitrile is added drop-wise by means of a dropping funnel in such a way that the temperature does not rise above 5° C. Thereafter, the ice bath is removed and the reaction mixture is stirred further for 30 min at room temperature. The reaction mixture is then stirred for 2 h at 60° C. After cooling to room temperature, the solid present is separated off. The filtrate is reduced until dry on the rotary evaporator and then absorbed in 100 ml acetone. Insoluble components are separated off and the filtrate is then reduced again under a vacuum until it is dry. The solid thus obtained is dried in a vacuum at 60° C.

Yield: 8.48 g (97%)

Elementary analysis: prov.: 55.48% C; 5.69% H; 14.38% N; 5.30°% P found: 55.57% C; 5.74% H; 14.11% N; 5.00% P.

Melting point: >250° C.

IR: $\tilde{\nu}$ (cm$^{-1}$)=3312 (w); 2928 (w); 1644 (m); 1595 (m); 1530 (m); 1480 (s); 1427 (m); 1367 (m); 1274 (m); 1252 (m); 1182 (s); 1132 (s); 1007 (s); 976 (vs); 914 (s); 860 (m); 777 (m); 755 (m); 683 (m); 606 (m); 553 (m)

$^1$H-NMR (500.13 MHz, DMSO-d$_6$): δ (ppm)=2.91 (s, 18H, CH$_3$); 7.11 (d, 6H, Ar—H, J$_{HH}$=8.7 Hz); 7.49 (d, 6H, Ar—H, $^3$J$_{HH}$=9.0 Hz); 8.37 (s, 3H, NH)

$^{13}$C-NMR (125.77 MHz, DMSO-d$_6$): δ (ppm)=36.20 (CH$_3$); 119.70 (d, Ar—C, $^3$J$_{PC}$=4.6 Hz); 120.98 (Ar—C); 138.41 (Ar—C); 144.29 (d, Ar—C, $^2$J$_{PC}$=7.3 Hz); 155.70 (C=O)

$^{31}$P-NMR (202.46 MHz, DMSO-d$_6$): δ (ppm)=−15.94 (O=P(OAr)$_3$)

Example 9: tri[o-(dimethylcarbamoylamino)phenyl]phosphate (HA-IX)

HA-IX corresponds to a compound according to Formula (I) with m=3; n=p=0; X=O; R$^1$=R$^2$=methyl; R$^6$=H, wherein the —NHC(O)NR$^1$R$^2$ group is in the o-position.

a) Production of N-(o-hydroxyphenyl)-N',N'-dimethylurea

The production of N-(o-hydroxyphenyl)-N',N'-dimethylurea takes place analogously to the production of N-(m-hydroxyphenyl)-N',N'-dimethylurea [see example 8 a)], wherein m-aminophenol is replaced by o-aminophenol (99%, Aldrich).

Yield: 34.70 g (56%)

Elementary analysis: prov.: 59.99% C; 6.71% H; 15.55% N found: 59.95% C; 6.62% H; 15.59% N.

Melting point: 137° C. (DSC-Onset), 139.5° C. (DSC-Peak)

IR: $\tilde{\nu}$ (cm$^{-1}$)=3430 (w); 3058 (w); 1644 (m); 1594 (m); 1538 (s); 1486 (s); 1451 (s); 1416 (s); 1366 (s); 1324 (s); 1280 (s); 1237 (s); 1201 (s); 1154 (m); 1103 (m); 1069 (m); 1030 (m); 923 (w); 889 (w); 807 (w); 748 (vs); 647 (w); 609 (m); 550 (s)

b) Production of HA-IX 8.11 g (45 mmol) N-(o-hydroxyphenyl)-N',N'-dimethylurea in 50 ml acetonitrile (100%, VWR) are prepared in an N$_2$-washed three-necked flask with a return condenser, dropping funnel, thermometer and magnetic stirrer, 4.55 g (45 mmol) triethylamine (99.5%, Sigma-Aldrich) are added and the reaction mixture being produced is cooled by means of an ice bath to a temperature of 0° C. A solution of 2.30 g (15 mmol) phosphoryl chloride (for synthesis, Merck) in 25 ml acetonitrile is added drop-wise by means of a dropping funnel in such a way that the temperature does not rise above 5° C. Thereafter, the ice bath is removed and the reaction mixture is stirred further for 30 min at room temperature. The reaction mixture is then stirred for 2 h at 60° C. After cooling to room temperature, the solid present is separated off and suspended in 50 ml water. The suspension is stirred for 1 h at room temperature, the solid is then separated off again, washed with water and dried at 60° C. in a vacuum.

Yield: 6.08 g (69%)

Elementary analysis: prov.: 55.48% C; 5.69% H; 14.38% N; 5.30% P found: 55.50% C; 5.57% H; 14.30% N; 5.07% P.

Melting point: 159° C. (DSC-Onset), 160° C. (DSC-Peak)

IR: $\tilde{\nu}$ (cm$^{-1}$)=3318 (w); 2924 (w); 1677 (m); 1637 (s); 1596 (m); 1525 (s); 1489 (s); 1439 (s); 1375 (s); 1296 (s); 1273 (s); 1251 (s); 1172 (vs); 1099 (s); 1067 (w); 1041 (m); 989 (s); 969 (vs); 936 (s); 887 (w); 847 (s); 750 (vs); 642 (m)

$^1$H-NMR (500.13 MHz, DMSO-d$_6$): δ (ppm)=2.74 (s, 18H, CH$_3$); 7.09 (m, 3H, Ar—H); 7.20 (t, 3H, Ar—H, $^3$J$_{HH}$=7.5 Hz); 7.28 (d, 3H, Ar—H, $^3$J$_{HH}$=8.0 Hz); 7.60 (d, 3H, Ar—H, J$_{HH}$=8.0 Hz); 7.81 (s, 3H, NH)

$^{13}$C-NMR (125.77 MHz, DMSO-d$_6$): δ (ppm)=35.85 (CH$_3$); 119.98 (d, Ar—C, $^3$J$_{PC}$=1.8 Hz); 124.35 (Ar—C); 125.70 (Ar—C); 131.22 (d, Ar—C, $^3$J$_{PC}$=6.4 Hz); 142.43 (d, Ar—C, $^2$J$_{PC}$=7.3 Hz); 155.47 (C=O)

$^{31}$P-NMR (202.46 MHz, DMSO-d$_6$): δ (ppm)=−16.72 (O=P(OAr)$_3$)

Example 10: tri[4-(dimethylcarbamoylamino)-3-methylphenyl]phosphate (HA-X)

HA-IX corresponds to a compound according to Formula (I) with m=3; n=p=0; X=O; R$^1$=R$^2$=R$^6$=methyl, wherein the —NHC(O)NR$^1$R$^2$ group is in the 4-position and R$^6$ is in the 3-position of the aromatic ring.

a) Production of N-(4-hydroxy-2-methylphenyl)-N',N'-dimethylurea

The production of N-(4-hydroxy-2-methylphenyl)-N',N'-dimethylurea takes place analogously to the production of N-(m-hydroxyphenyl)-N',N'-dimethylurea [see example 8 a)], wherein m-aminophenol is replaced by 4-amino-3-methylphenol (98%, Alfa-Aesar).

Yield: 16.17 g (59%)

Elementary analysis: prov.: 61.84% C; 7.27% H; 14.42% N found: 61.75% C; 7.12% H; 14.29% N.

Melting point: 221° C. (DSC-Onset), 227° C. (DSC-Peak)

IR: $\tilde{\nu}$ (cm$^{-1}$)=3354 (w); 3161 (w); 2923 (w); 1591 (m); 1531 (s); 1461 (s); 1372 (m); 1294 (m); 1225 (vs): 1191 (m); 1158 (m); 1101 (m); 1064 (m); 1041 (w); 1002 (w); 951 (w); 880 (m); 815 (m); 752 (s); 630 (w); 556 (m)

b) Production of HA-X 6.41 g (33 mmol) N-(4-hydroxy-2-methylphenyl)-N',N'-dimethylurea in 40 ml acetonitrile (100%, VWR) are prepared in an N$_2$-washed three-necked flask with a return condenser, dropping funnel, thermometer and magnetic stirrer, 3.34 g (33 mmol) triethylamine (99.5%, Sigma-Aldrich) are added and the reaction mixture being produced is cooled by means of an ice bath to a temperature of 0° C. A solution of 1.69 g (11 mmol) phosphoryl chloride (for synthesis, Merck) in 15 ml acetonitrile is added drop-wise by means of a dropping funnel in such a way that the temperature does not rise above 5° C. Thereafter, the ice bath is removed and the reaction mixture is stirred further for 30 min at room temperature. The reaction mixture is then stirred for 2 h at 60° C. After cooling to room temperature, the solid present is separated off. The filtrate is reduced on the rotary evaporator until it is dry and then absorbed in 30 ml acetone. Insoluble components are separated off and the filtrate is then reduced again under a vacuum until it is dry. The solid thus obtained is dried in a vacuum at 60° C.

Yield: 5.58 g (81%)

Elementary analysis: prov.: 57.50% C; 6.27% H; 13.41% N; 4.94% P found: 57.34% C; 6.23% H; 12.78% N; 4.52% P.

Melting point: >250° C.

IR: $\tilde{v}$ (cm$^{-1}$)=3287 (w); 2927 (w); 1639 (m); 1494 (s); 1412 (m); 1366 (m); 1291 (m); 1267 (m); 1199 (s); 1143 (vs); 1111 (m); 1067 (w); 1007 (s); 968 (vs); 914 (m); 893 (m); 869 (m); 812 (m); 758 (m); 708 (w); 600 (m); 558 (m)

$^1$H-NMR (500.13 MHz, DMSO-d$_6$): δ (ppm)=2.91 (s, 18H, CH$_3$); 7.11 (d, 6H, Ar—H, $^3J_{HH}$=8.7 Hz); 7.49 (d, 6H, Ar—H, $^3J_{HH}$=9.0 Hz); 8.37 (s, 3H, NH)

$^{13}$C-NMR (125.77 MHz, DMSO-d$_6$): δ (ppm)=36.20 (CH$_3$); 119.70 (d, Ar—C, $^3J_{PC}$=4.6 Hz); 120.98 (Ar—C); 138.41 (Ar—C); 144.29 (d, Ar—C, $^2J_{PC}$=7.3 Hz); 155.70 (C=O)

$^{31}$P-NMR (202.46 MHz, DMSO-d$_6$): δ (ppm)=−15.94 (O=P(OAr)$_3$)

3) Epoxy Resin Compositions with Hardeners/Cure Accelerants According to the Invention and Preparation of the Formulations The invention will be shown using the example of the formulations of epoxy resin compositions listed in Table 1.

TABLE 1

Epoxy resin compositions used

| Example (according to the invention) | Components of the formulation (parts by weight) | | |
|---|---|---|---|
| A (no) | ER (100) | HA (8) | |
| B (yes) | ER (100) | HA-I (8) | |
| C (no) | ER (100) | H (6.5) | HA (3) |
| D (yes) | ER (100) | H (6.5) | HA-I (3) |
| E (yes) | ER (100) | H (6.5) | HA-III (5) |
| F (yes) | ER (100) | H (6.5) | HA-IV (5) |
| G (yes) | ER (100) | H (6.5) | HA-V (5) |
| H (yes) | ER (100) | H (6.5) | HA-VI (5) |
| I (yes) | ER (100) | H (6.5) | HA-VII (5) |
| J (yes) | ER (100) | HA-III (8) | |
| K (yes) | ER (100) | HA-IV (8) | |
| L (yes) | ER (100) | HA-VI (8) | |

The components mentioned under the respective example are thoroughly mixed with one another in a mortar for DSC investigations and determinations of latencies.

For investigations on the flame retardancy effect, the individual components of a formulation are mixed in a dissolver. For this purpose, the components are weighed into a 1-L dissolver vessel and the mixture is dispersed in the dissolver for 2 min at 900 rpm, thereafter for 2 min at 3,000 rpm and finally for 3 min at 3,500 rpm. Thereafter, the mixture is degassed for 60 min at 60 rpm under vacuum. The formulation is ready for use when no further discernible bubbles are located on the surface.

Produced from the formulations thus produced are cured plates with the dimensions 4 mm×180 mm×350 mm, from which the test specimens required for the investigations on combustion behaviour are milled using a CNC milling machine. The conditions used for the production of the plates (1st step: curing, 2nd step: annealing) for the individual formulations are given in Table 2.

TABLE 2

Conditions for producing cured plates of the exemplary formulations

| Example (according to the invention) | Curing | | Annealing | |
|---|---|---|---|---|
| | Temperature [° C.] | Time [h] | Temperature [° C.] | Time [h] |
| A (no) | 95 | 3 | 100 | 2 |
| B (yes) | 100 | 4 | 115 | 2 |
| C (no) | 100 | 2 | 140 | 2 |
| D (yes) | 100 | 2.5 | 140 | 2 |
| E (yes) | 95 | 2.5 | 130 | 2 |
| F (yes) | 105 | 3 | 140 | 2 |
| G (yes) | 115 | 3 | 125 | 2 |

4) DSC Investigations

The effectiveness of the compounds according to the invention as hardeners/cure accelerants is shown using the example of HA-I compared to HA, a common hardener/cure accelerant.

For this purpose, characteristic data from DSC measurements are used. The DSC measurements described below are carried out on a dynamic thermal flow difference calorimeter DSC 1 or DSC 822e (Mettler Toledo)

a) Dynamic DSC:

A sample of the formulation is heated at a heating rate of 10 K/min from 30-250° C. The exothermic reaction peak is evaluated by determining the onset temperature (T$_{onset}$), the temperature at the peak maximum (T$_{max}$) and the peak area as a measure of the released reaction heat (Δ$_R$H).

b) T$_G$ Determination:

To determine the maximum glass transition temperature (End-T$_G$), a sample of the cured formulation is subjected to the following DSC temperature program: heating from 30-200° C. at 20 K/min, 10 min holding at 200° C., cooling from 200-50° C. at 20 K/min, 5 min holding at 50° C., heating from 50-200° C. at 20 K/min, 10 min holding at 200° C., cooling from 200-50° C. at 20 K/min, 5 min holding at 50° C., heating from 50-220° C. at 20 K/min. From the two last heating cycles, the glass transition temperature is determined and the average given as End-T$_G$, in each case, by placing a tangent at the turning point of the greatest change in the thermal capacity (ΔC$_p$).

c) Isothermal DSC:

A sample of the formulation is kept constant at the given temperature for the given time (isothermal curing of the formulation). The evaluation takes place by determining the time of the peak maximum (as a measure for the start of the curing process) and the 90% conversion (as a measure of the end of the curing process) of the exothermal reaction peak.

The results of the DSC investigations are summarised in Table 3 and Table 4.

TABLE 3

Results of the dynamic DSC und T$_G$ determination

| Example (according to the invention) | T$_{onset}$ [° C.] | T$_{max}$ [° C.] | Δ$_R$H [J/g] | End-T$_G$ [° C.] |
|---|---|---|---|---|
| A (no) | 153 | 175 | 544 | 98 |
| B (yes) | 156 | 181 | 543 | 111 |

TABLE 3-continued

Results of the dynamic DSC und $T_G$ determination

| Example (according to the invention) | $T_{onset}$ [° C.] | $T_{max}$ [° C.] | $\Delta_R H$ [J/g] | End-$T_G$ [° C.] |
|---|---|---|---|---|
| C (no) | 137 | 144 | 477 | 137 |
| D (yes) | 145 | 153 | 509 | 147 |
| E (yes) | 143 | 152 | 475 | 137 |
| F (yes) | 151 | 159 | 457 | 142 |
| G (yes) | 150 | 170 | 575 | 136 |
| H (yes) | 148 | 157 | 483 | 136 |
| I (yes) | 150 | 159 | 451 | 136 |
| J (yes) | 154 | 177 | 355 | 112 |
| K (yes) | 152 | 176 | 223 | 98 |
| L (yes) | 162 | 185 | 256 | 100 |

TABLE 4

Results of the isothermal DSC

| Example (according to the invention) | Conditions | Peak maximum [min] | 90% conversion [min] |
|---|---|---|---|
| A (no) | 140° C., 120 min | 7.5 | 26.5 |
| B (yes) | 140° C., 120 min | 9.4 | 47.8 |
| C (no) | 140° C., 60 min | 1.4 | 12.5 |
| D (yes) | 140° C., 60 min | 2.7 | 11.9 |
| E (yes) | 140° C., 60 min | 2.5 | 13.2 |
| F (yes) | 140° C., 60 min | 3.9 | 17.2 |
| G (yes) | 140° C., 180 min | 4.4 | 73.3 |
| H (yes) | 140° C., 60 min | 3.2 | 18.9 |
| I (yes) | 140° C., 60 min | 4.0 | 23.0 |
| J (yes) | 140° C., 60 min | 8.3 | 35.9 |
| K (yes) | 140° C., 90 min | 7.2 | 51.6 |
| L (yes) | 140° C., 120 min | 9.3 | 65.9 |

The comparison of the examples according to the invention with a technically conventional hardener/cure accelerant such as HA (examples A and C) shows that when using the hardeners or cure accelerants according to the invention, comparable characteristic values for the curing process can be determined by means of DSC. The values for $T_{onset}$ and $T_{max}$ from the dynamic DSC measurements for formulations with the hardeners/cure accelerants according to the invention are slightly higher than when using HA (examples A or C), i.e. the curing is slightly slower when using the hardeners/cure accelerants according to the invention. The energy $\Delta_R H$ being released during the curing is in the same order of magnitude in all formulations, which shows that in all the formulations tested, a curing actually takes place. When using the hardeners/cure accelerants according to the invention, the achievable glass transition temperature compared to the respective formulation with the technically conventional hardener/cure accelerant is at least comparable and in some examples significantly higher (examples B, D, F, J and L).

In the isothermal DSC measurements, the results are also comparable. The peak maximum in isothermal curing in the formulations according to the invention is reached slightly later but these differences are not significant. The time up to a reaction conversion of 90% when using the hardeners/cure accelerants according to the invention compared to the technically conventional hardener/cure accelerant HA is sometimes slightly longer, but technically still feasible.

To summarise, the DSC investigations show that the compounds according to the invention can be used analogously to already known hardeners/cure accelerants and show a similar curing characteristic here.

5) Flame Retardancy Effect

The flame retardancy effect of the compounds according to the invention is shown using the example of HA-I compared to HA, a common hardener/cure accelerant. Test specimens of cured formulations are used for the investigations mentioned below. The following fire tests are carried out:

a) Oxygen Index:

The oxygen index (also limiting oxygen index, LOI) is determined according to DIN EN ISO 4589-2 (Plastics materials—Determination of the combustion behaviour by the oxygen index—Part 2: Testing at ambient temperature). The tests are carried out using test specimens with the dimension 100 mm×10 mm×4 mm (test specimen type III) by ignition method A.

b) Small Burner Test:

The small burner test takes place according to UL 94 V (Tests for Flammability of Plastic Materials for Parts in Devices and Applications). The tests are carried out each with 5 test specimens with the dimension 127 mm×13 mm×4 mm.

The results of the individual fire tests are summarised in Table 5 and Table 6.

TABLE 5

Results of the oxygen index determinations

| Example (according to the invention) | Oxygen index [% by volume] |
|---|---|
| A (no) | 21.1 |
| B (yes) | 26.7 |
| C (no) | 20.7 |
| D (yes) | 22.3 |
| E (yes) | 23.2 |
| F (yes) | 23.0 |
| G (yes) | 22.3 |

The oxygen index states what oxygen content (in % by volume) is at least required in an oxygen-nitrogen gas mixture so that an ignited test specimen continues to burn after removal of the ignition source. If the oxygen index is greater than the oxygen content present in the normal atmosphere of about 21% by volume, a self-extinguishing of the tested materials is observed and therefore a flame-retarding effect is shown. For the materials corresponding to examples A and C (not according to the invention) oxygen index values of 21.1 vol. % or 20.7 vol. % were determined. In the normal atmosphere (oxygen content about 21 vol. %) a continuing further burning after the ignition by means of a burner flame is established here. A higher value is determined for examples D, E, F and G (according to the invention, containing HA-I, HA-III, HA-IV or HA-V as cure accelerants). The best result is determined for example B (according to the invention, containing HA-I as the hardener) with 26.7 vol. %. In the materials mentioned last, a rapid self-extinguishing is to be expected in the normal atmosphere (air).

TABLE 6

Results of the small burner tests (5 test specimens each)

| Example (according to the invention) | Afterburn duration 1st flame treatment [s]* | Afterburn duration 2nd. flame treatment [s]* | Observation# |
|---|---|---|---|
| A (no) | >180/>180/>180/>180/>180 | —/—/—/—/— | burning dripping off with ignition of the wadding and complete combustion |
| B (yes) | 16/5/5/15/5 | 207/32/2/28/109 | self-extinguishing without falling away |
| C (no) | 2/>180/>180/3/>180 | >180/—/—/>180/— | burning dripping off with ignition of the wadding and complete combustion |
| D (yes) | 74/166/>180/2/5 | >180/—/—/77/184 | partial burning falling away with ignition of the wadding and complete combustion, partly self-extinguishing without falling away |

*Given in each case are the results of the 5 individual test specimens. A second flame treatment only takes place when self-extinguishing is observed during the first flame treatment. In the case of complete combustion without self-extinguishing, >180 s is noted as the value for the afterburn duration.
The observations relate to the state after two flame treatments. If only one flame treatment was carried out, the state present thereafter is described.

The flame treatment tests of the small burner test according to UL 94 V show an improvement in the flame retardancy effect when using the hardener/cure accelerant HA-I according to the invention instead of the technically conventional hardener/cure accelerant HA. Both for example A and example C (neither according to the invention), the afterburn duration in the individual tests is predominantly more than 180 s and a burning dripping off (with ignition of the wadding located therebelow) and a complete combustion of the test specimens is to be observed. For examples B and D (both according to the invention, containing HA-I as the hardener or cure accelerant), the afterburn duration in the individual tests is predominantly less than 180 s and in some cases even significantly less (formulation B). The test specimens of formulation B, in contrast to formulation A, show self-extinguishing without dripping off or the falling away of test specimen parts. For the test specimens of formulation D, a burning falling away (with ignition of the wadding located therebelow) and complete combustion was partly observed, but some of the test specimens also exhibited self-extinguishing without dripping off or the falling away of test specimen parts. Compared to the analogous formulation C (containing HA as the cure accelerant), an improved flame retardancy effect is thus also to be seen for formulation D (containing HA-I as the cure accelerant).

To summarise, the investigations show that the compound HA-I according to the invention when used as the sole hardener or as the cure accelerant, in comparison with the technically conventional hardener/cure accelerant HA, leads to an improvement in the flame retardancy effect within an otherwise comparable epoxy resin composition. The use of the hardener/cure accelerant HA-I according to the invention in examples B and D instead of a technically conventional hardener such as HA (examples A and C) within an epoxy resin composition leads both to improvement of the oxygen index and to an improved combustion behaviour in the small burner test. For the compounds HA-III (example E), HA-IV (example F) and HA-V (example G) during use as the sole hardener, a higher oxygen index was also determined compared to the technically conventional hardener HA (example). Therefore an improved flame retardancy effect is demonstrated analogously to the compound HA-I (example D).

6) Latencies (Storage Stability)

To determine the latency (storage stability) about 20 g of the respective formulation according to Table 1 are freshly prepared and then stored at a temperature of 23° C. and a relative humidity of 50% (climatic chamber). By regularly measuring the dynamic viscosity, the progressing cross-linking (curing) of the formulation under these storage conditions is recorded. The dynamic viscosity is determined using a Haake viscosimeter [cone(1°)-plate method, measurement at 25° C., shear rate 5.0 s$^{-1}$]. A formulation is classified as stable when stored (still suitable for processing) until the viscosity doubles.

TABLE 7

Results of the test for storage stability

| Example (according to the invention) | Time until the dynamic viscosity [d] doubles |
|---|---|
| A (no) | 32 |
| B (yes) | 70 |
| C (no) | 30 |
| D (yes) | 70 |
| E (yes) | 150 |
| F (yes) | >80 |
| G (yes) | >120 |
| H (yes) | >60 |
| I (yes) | >120 |
| J (yes) | 130 |
| K (yes) | >80 |
| L (yes) | >60 |

The formulations according to the invention, at at least 60 days, have a significantly higher storage stability than the comparable formulations not according to the invention at a storage stability of 32 days (formulation A) or 30 days (formulation C).

To summarise, the tests for storage stability show that using the compounds according to the invention, formulations can be obtained which, compared to formulations that are obtained using conventional hardeners or cure accelerants, have a significantly better storage stability.

The invention claimed is:
1. A composition comprising at least one compound from the group of esters of phosphorus-containing acids according to Formula (I)

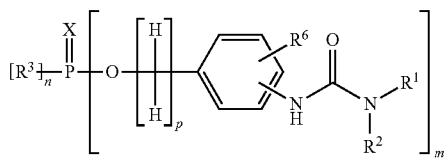

Formula (I)

wherein radicals $R^1$, $R^2$, $R^3$, $R^6$, X and indices m, n, p, simultaneously or independently are:
- $R^1$, $R^2$=simultaneously or independently of one another, alkyl,
- $R^3$=alkyl, aryl, —O-aryl, —O-alkylaryl or —O-arylalkyl,
- $R^6$=hydrogen, alkyl or —NHC(O)$NR^1R^2$,
- X=oxygen or sulphur,
- m=1, 2 or 3,
- n=0, 1 or 2, wherein m+n=3, and
- p=0, 1 or 2.

2. The composition of claim 1, wherein the compound is selected from the group of phosphoric acid esters or thiophosphoric acid esters according to Formula (I), wherein $R^1$, $R^2$, $R^3$, $R^6$, X and indices m, n, p, simultaneously or independently of one another are:
- $R^1$, $R^2$=simultaneously or independently of one another, alkyl,
- $R^3$=—O-aryl, —O-alkylaryl or —O-arylalkyl,
- $R^6$=hydrogen, alkyl or —NHC(O)$NR^1R^2$,
- X=sulphur or oxygen,
- m=1, 2 or 3,
- n=0, 1 or 2, wherein m+n=3, and
- p=0, 1 or 2.

3. The composition of claim 1, wherein the compound is selected from the group of phosphonates or thiophosphonates according to Formula (I), wherein the radicals $R^1$, $R^2$, $R^3$, $R^6$, X and the indices m, n, p, simultaneously or independently of one another are:
- $R^1$, $R^2$=simultaneously or independently of one another, alkyl,
- $R^3$=alkyl or aryl,
- $R^6$=hydrogen, alkyl or —NHC(O)$NR^1R^2$,
- X=sulphur or oxygen,
- m=2,
- n=1, and
- p=0, 1 or 2.

4. The composition of claim 1, wherein the compound is selected from the group of phosphinates or thiophosphinates according to Formula (I), wherein the radicals $R^1$, $R^2$, $R^3$, $R^6$, X and the indices m, n, p, simultaneously or independently of one another are:
- $R^1$, $R^2$=simultaneously or independently of one another, alkyl,
- $R^3$=alkyl or aryl,
- $R^6$=hydrogen, alkyl or —NHC(O)$NR^1R^2$,
- X=sulphur or oxygen,
- m=1,
- n=2, and
- p=0, 1 or 2.

5. The composition of claim 1, wherein the radicals $R^1$, $R^2$, $R^3$, $R^6$, X and the index p in Formula (I), simultaneously or independently of one another are:
- $R^1$, $R^2$=simultaneously or independently of one another, methyl or ethyl,
- $R^3$=—O-Aryl,
- $R^6$=hydrogen or alkyl,
- X=sulphur or oxygen, and
- p=0.

6. The composition of claim 1, wherein the radicals $R^1$, $R^2$, $R^3$, $R^6$, X and the index p in Formula (I), simultaneously or independently of one another are:
- $R^1$, $R^2$=simultaneously or independently of one another, methyl or ethyl,
- $R^3$=aryl,
- $R^6$=hydrogen or alkyl,
- X=sulphur or oxygen, and
- p=0.

7. A composition comprising at least two different compounds of claim 1.

8. A composition comprising:
a) at least one compound for curing epoxy resins, which is different from a compound recited in claim 1; and,
b) a compound recited in claim 1.

9. An epoxy resin composition comprising:
a) at least one epoxy resin; and,
b) at least one compound from the group of esters of phosphorus-containing acids according to Formula (I)

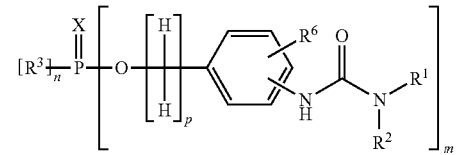

Formula (I)

wherein radicals $R^1$, $R^2$, $R^3$, $R^6$, X and indices m, n, p, simultaneously or independently are:
- $R^1$, $R^2$=simultaneously or independently of one another, alkyl,
- $R^3$=alkyl, aryl, —O-aryl, —O-alkylaryl or —O-arylalkyl,
- $R^6$=hydrogen, alkyl or —NHC(O)$NR^1R^2$,
- X=oxygen or sulphur,
- m=1, 2 or 3,
- n=0, 1 or 2, wherein m+n=3, and
- p=0, 1 or 2.

10. A composite material comprising:
a) a carrier material;
b) at least one epoxy resin; and,
c) at least one compound from the group of esters of phosphorus-containing acids according to Formula (I)

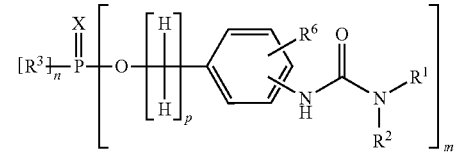

Formula (I)

wherein radicals $R^1$, $R^2$, $R^3$, $R^6$, X and indices m, n, p, simultaneously or independently are:
- $R^1$, $R^2$=simultaneously or independently of one another, alkyl,
- $R^3$=alkyl, aryl, —O-aryl, —O-alkylaryl or —O-arylalkyl, R⁶=hydrogen, alkyl or —NHC(O)NR¹R²,
X=oxygen or sulphur,
m=1, 2 or 3,
n=0, 1 or 2, wherein m+n=3, and
p=0, 1 or 2.

11. A method for curing prepregs, laminates, coatings, polymer resin mixtures, powder paints, sealing compounds or adhesives, in each case comprising applying a compound from the group of esters of phosphorus-containing acids according to Formula (I)

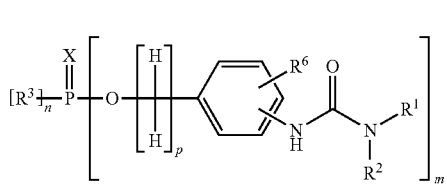

Formula (I)

wherein radicals R¹, R², R³, R⁶, X and indices m, n, p, simultaneously or independently are:
R¹, R²=simultaneously or independently of one another, alkyl,
R³=alkyl, aryl, —O-aryl, —O-alkylaryl or —O-arylalkyl,
R⁶=hydrogen, alkyl or —NHC(O)NR¹R²,
X=oxygen or sulphur,
m=1, 2 or 3,
n=0, 1 or 2, wherein m+n=3, and
p=0, 1 or 2
to the prepregs, laminates, coatings, polymer resin mixtures, powder paints, sealing compounds or adhesives, and
wherein the prepregs, laminates, coatings, polymer resin mixtures, powder paints, sealing compounds or adhesives are cured.

12. A method for accelerated curing of prepregs, laminates, coatings, polymer resin mixtures, powder paints, sealing compounds or adhesives, in each case comprising applying a compound from the group of esters of phosphorus-containing acids according to Formula (I)

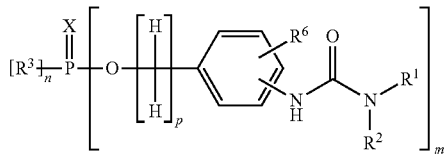

Formula (I)

wherein radicals R¹, R², R³, R⁶, X and indices m, n, p, simultaneously or independently are:
R¹, R²=simultaneously or independently of one another, alkyl,
R³=alkyl, aryl, —O-aryl, —O-alkylaryl or —O-arylalkyl,
R⁶=hydrogen, alkyl or —NHC(O)NR¹R²,
X=oxygen or sulphur,
m=1, 2 or 3,
n=0, 1 or 2, wherein m+n=3, and
p=0, 1 or 2
to the prepregs, laminates, coatings, polymer resin mixtures, powder paints, sealing compounds or adhesives, and wherein the prepregs, laminates, coatings, polymer resin mixtures, powder paints, sealing compounds or adhesives undergo accelerated curing.

13. A flame retardant composition comprising at least one compound from the group of esters of phosphorus-containing acids according to Formula (I)

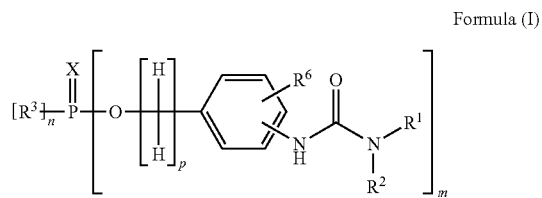

Formula (I)

wherein radicals R¹, R², R³, R⁶, X and indices m, n, p, simultaneously or independently are:
R¹, R²=simultaneously or independently of one another, alkyl,
R³=alkyl, aryl, —O-aryl, —O-alkylaryl or —O-arylalkyl,
R⁶=hydrogen, alkyl or —NHC(O)NR¹R²,
X=oxygen or sulphur,
m=1, 2 or 3,
n=0, 1 or 2, wherein m+n=3, and
p=0, 1 or 2.

14. A hardener composition comprising at least one compound from the group of esters of phosphorus-containing acids according to Formula (I)

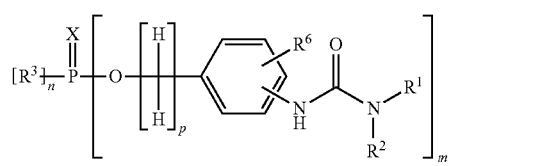

Formula (I)

wherein radicals R¹, R², R³, R⁶, X and indices m, n, p, simultaneously or independently are:
R¹, R²=simultaneously or independently of one another, alkyl,
R³=alkyl, aryl, —O-aryl, —O-alkylaryl or —O-arylalkyl,
R⁶=hydrogen, alkyl or —NHC(O)NR¹R²,
X=oxygen or sulphur,
m=1, 2 or 3,
n=0, 1 or 2, wherein m+n=3, and
p=0, 1 or 2 wherein the hardener composition can be provided as a single-component paste.

15. A cure accelerator composition comprising at least one compound from the group of esters of phosphorus-containing acids according to Formula (I)

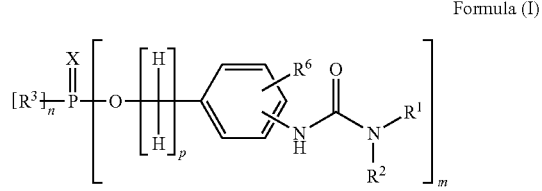

Formula (I)

wherein radicals $R^1$, $R^2$, $R^3$, $R^6$, X and indices m, n, p, simultaneously or independently are:
$R^1$, $R^2$=simultaneously or independently of one another, alkyl,
$R^3$=alkyl, aryl, —O-aryl, —O-alkylaryl or —O-arylalkyl,
$R^6$=hydrogen, alkyl or —NHC(O)NR$^1$R$^2$,
X=oxygen or sulphur,
m=1, 2 or 3,
n=0, 1 or 2, wherein m+n=3, and
p=0, 1 or 2
wherein the hardener composition can be provided as a single-component paste.

16. A method for curing an epoxy resin comprising applying to the epoxy resin a compound from the group of esters of phosphorus-containing acids according to Formula (I)

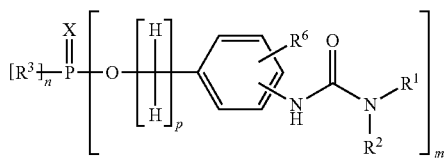

Formula (I)

wherein radicals $R^1$, $R^2$, $R^3$, $R^6$, X and indices m, n, p, simultaneously or independently are:
$R^1$, $R^2$=simultaneously or independently of one another, alkyl,
$R^3$=alkyl, aryl, —O-aryl, —O-alkylaryl or —O-arylalkyl,
$R^6$=hydrogen, alkyl or —NHC(O)NR$^1$R$^2$,
X=oxygen or sulphur,
m=1, 2 or 3,
n=0, 1 or 2, wherein m+n=3, and
p=0, 1 or 2
wherein the epoxy resin is cured.

17. A method for accelerated curing of an epoxy resin comprising applying to the epoxy resin a compound from the group of esters of phosphorus-containing acids according to Formula (I)

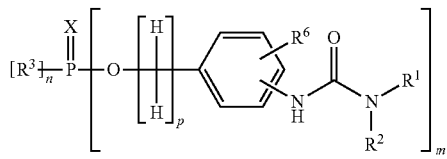

Formula (I)

wherein radicals $R^1$, $R^2$, $R^3$, $R^6$, X and indices m, n, p, simultaneously or independently are:
$R^1$, $R^2$=simultaneously or independently of one another, alkyl,
$R^3$=alkyl, aryl, —O-aryl, —O-alkylaryl or —O-arylalkyl,
$R^6$=hydrogen, alkyl or —NHC(O)NR$^1$R$^2$,
X=oxygen or sulphur,
m=1, 2 or 3,
n=0, 1 or 2, wherein m+n=3, and
p=0, 1 or 2
wherein the epoxy resin undergoes accelerated curing.

* * * * *